United States Patent
Mortarino

(10) Patent No.: US 9,204,954 B2
(45) Date of Patent: Dec. 8, 2015

(54) KNITTED SCAFFOLD WITH DIAGONAL YARN

(75) Inventor: Enrico Mortarino, Hickory, NC (US)

(73) Assignee: Allergan, Inc., Irvine, CA (US)

( * ) Notice: Subject to any disclaimer, the term of this patent is extended or adjusted under 35 U.S.C. 154(b) by 326 days.

(21) Appl. No.: 13/093,651

(22) Filed: Apr. 25, 2011

(65) Prior Publication Data

US 2011/0224703 A1    Sep. 15, 2011

Related U.S. Application Data

(63) Continuation-in-part of application No. 12/680,404, filed as application No. PCT/US2009/063717 on Nov. 9, 2009.

(60) Provisional application No. 61/122,520, filed on Dec. 15, 2008.

(51) Int. Cl.
*A61F 2/00* (2006.01)
*A61F 2/12* (2006.01)
(Continued)

(52) U.S. Cl.
CPC ............... *A61F 2/0063* (2013.01); *A61F 2/12* (2013.01); *A61L 27/3604* (2013.01); *D04B 1/22* (2013.01); *D04B 21/08* (2013.01); *D04B 21/12* (2013.01); *A61F 2002/0068* (2013.01); *D10B 2509/08* (2013.01)

(58) Field of Classification Search
CPC ........... A61F 2/0063; A61F 2/12; A61F 2/90; D04B 1/22; D04B 21/00; D04B 21/12; D04B 21/14; D04B 21/145; D04B 21/16; D04B 21/165; D04B 21/18; D04B 21/08
USPC ........ 606/151; 623/23.72, 23.74; 66/191–195
See application file for complete search history.

(56) References Cited

U.S. PATENT DOCUMENTS

| 848,605 | A | | 3/1907 | Schmic |
| 955,541 | A | * | 4/1910 | Petersen .................... 139/387 R |

(Continued)

FOREIGN PATENT DOCUMENTS

| DE | 3917174 | 12/1990 |
| DE | 19928635 | 10/2000 |

(Continued)

OTHER PUBLICATIONS

Altman et al., Silk based biomaterials, *Biomaterials* (2003) 24:401-416.

(Continued)

*Primary Examiner* — Dianne Dornbusch
(74) *Attorney, Agent, or Firm* — Linda Allyson Nassif

(57) ABSTRACT

A knitted scaffold comprising at least two silk yarns in a knit direction and a yarn member diagonal to the knit direction to thereby provide a knitted fabric or mesh for surgical use that can retain its shape and/or resist collapse when opposing forces are applied at an angle from the knit direction. The knitted scaffold may include at least two yarns laid in a knit direction and engaging each other to define a plurality of nodes. The at least two yarns can include a first yarn and a second yarn extending between and forming loops about two nodes. The second yarn has a higher tension at the two nodes than the first yarn. The second yarn substantially prevents the first yarn from moving at the two nodes and substantially prevents the knitted mesh from unraveling at the nodes.

6 Claims, 35 Drawing Sheets

(51) Int. Cl.
*A61L 27/36* (2006.01)
*D04B 1/22* (2006.01)
*D04B 21/08* (2006.01)
*D04B 21/12* (2006.01)

(56) References Cited

U.S. PATENT DOCUMENTS

| | | | |
|---|---|---|---|
| 1,300,696 A * | 4/1919 | Branson | 66/193 |
| 1,709,662 A | 4/1929 | George | |
| 1,815,279 A | 7/1931 | Takamine., Jr | |
| 1,828,736 A | 10/1931 | Norman, Jr. | |
| 1,896,494 A | 2/1933 | Myers et al. | |
| 1,921,022 A | 9/1933 | Fink et al. | |
| 1,990,588 A | 2/1935 | Fink et al. | |
| 2,040,949 A | 5/1936 | Olpin et al. | |
| 3,314,123 A * | 4/1967 | Groebli | 28/165 |
| 3,552,154 A * | 1/1971 | Lesley | 66/192 |
| 3,595,276 A | 7/1971 | Wrzesieo | |
| 3,672,187 A * | 6/1972 | Simpson | 66/192 |
| 3,922,888 A * | 12/1975 | Patterson | 66/192 |
| 3,931,721 A * | 1/1976 | Adamson | 66/195 |
| 3,952,555 A * | 4/1976 | Lesley | 66/195 |
| 3,999,407 A * | 12/1976 | Odham | 66/193 |
| 4,089,071 A * | 5/1978 | Kalnberz et al. | 623/23.61 |
| 4,118,842 A | 10/1978 | Norris et al. | |
| 4,141,207 A | 2/1979 | Mizushima et al. | |
| 4,248,064 A * | 2/1981 | Odham | 66/192 |
| 4,340,091 A * | 7/1982 | Skelton et al. | 139/383 R |
| 4,388,364 A * | 6/1983 | Sanders | 442/313 |
| 4,518,640 A * | 5/1985 | Wilkens | 428/102 |
| 4,530,113 A * | 7/1985 | Matterson | 623/1.51 |
| 4,792,336 A | 12/1988 | Hlavacek et al. | |
| 4,816,028 A * | 3/1989 | Kapadia et al. | 623/1.52 |
| 4,942,875 A | 7/1990 | Hlavacek et al. | |
| 4,984,570 A * | 1/1991 | Langen et al. | 602/44 |
| 5,120,829 A | 6/1992 | Pierschbacher et al. | |
| 5,134,006 A * | 7/1992 | Irvin | 428/68 |
| 5,171,505 A | 12/1992 | Lock | |
| 5,178,630 A * | 1/1993 | Schmitt | 623/1.52 |
| 5,191,777 A * | 3/1993 | Schnegg | 66/195 |
| 5,250,077 A | 10/1993 | Fuse et al. | |
| 5,252,285 A | 10/1993 | Lock | |
| 5,366,504 A * | 11/1994 | Andersen et al. | 623/1.5 |
| 5,385,836 A | 1/1995 | Kimura et al. | |
| 5,456,697 A | 10/1995 | Chesterfield et al. | |
| 5,490,602 A * | 2/1996 | Wilson et al. | 216/56 |
| 5,509,931 A * | 4/1996 | Schmitt | 623/1.52 |
| 5,569,273 A | 10/1996 | Titone et al. | |
| 5,587,456 A | 12/1996 | Pierschbacher et al. | |
| 5,591,822 A | 1/1997 | Pierschbacher et al. | |
| 5,598,615 A | 2/1997 | Takada | |
| 5,606,019 A | 2/1997 | Cappello | |
| 5,674,276 A * | 10/1997 | Andersen et al. | 623/1.5 |
| 5,760,176 A | 6/1998 | Pierschbacher et al. | |
| 5,771,716 A | 6/1998 | Schlussel | |
| 5,795,835 A * | 8/1998 | Bruner et al. | 442/310 |
| 5,849,040 A | 12/1998 | Kanehisa | |
| 5,919,232 A | 7/1999 | Chaffringeon et al. | |
| 5,951,506 A | 9/1999 | Tsubouchi | |
| 5,990,378 A | 11/1999 | Ellis | |
| 6,004,888 A * | 12/1999 | Sugimoto et al. | 442/60 |
| 6,006,552 A * | 12/1999 | Matsuda et al. | 66/193 |
| 6,042,592 A * | 3/2000 | Schmitt | 606/151 |
| 6,074,722 A * | 6/2000 | Cuccias | 428/107 |
| 6,076,448 A * | 6/2000 | Rexroad | 87/12 |
| 6,090,116 A | 7/2000 | D'Aversa et al. | |
| 6,110,590 A | 8/2000 | Zarkoob et al. | |
| 6,113,623 A | 9/2000 | Sgro | |
| 6,136,022 A * | 10/2000 | Nunez et al. | 623/1.1 |
| 6,146,418 A | 11/2000 | Berman | |
| 6,164,339 A * | 12/2000 | Greenhalgh | 139/1 R |
| 6,171,984 B1 * | 1/2001 | Paulson et al. | 442/331 |
| 6,175,053 B1 | 1/2001 | Tsubouchi | |
| 6,228,132 B1 | 5/2001 | Prince et al. | |
| 6,233,978 B1 * | 5/2001 | Gehring et al. | 66/195 |
| 6,287,316 B1 * | 9/2001 | Agarwal et al. | 606/151 |
| 6,287,340 B1 | 9/2001 | Altman et al. | |
| 6,302,922 B1 | 10/2001 | Kanehisa | |
| 6,303,136 B1 | 10/2001 | Li et al. | |
| 6,389,851 B1 * | 5/2002 | Groshens | 66/192 |
| 6,408,656 B1 | 6/2002 | Ory et al. | |
| 6,440,740 B1 | 8/2002 | Tsubouchi et al. | |
| 6,443,964 B1 | 9/2002 | Ory et al. | |
| 6,540,773 B2 * | 4/2003 | Dong | 623/1.13 |
| 6,592,617 B2 * | 7/2003 | Thompson | 623/1.53 |
| 6,638,284 B1 | 10/2003 | Rousseau et al. | |
| 6,729,356 B1 | 5/2004 | Baker et al. | |
| 6,737,371 B1 | 5/2004 | Planck et al. | |
| 6,773,459 B2 | 8/2004 | Dauner et al. | |
| 6,783,554 B2 | 8/2004 | Amara et al. | |
| 6,827,743 B2 * | 12/2004 | Eisermann et al. | 623/23.54 |
| 6,848,281 B2 | 2/2005 | Ishihara et al. | |
| 6,856,715 B1 * | 2/2005 | Ebbesen et al. | 385/14 |
| 6,866,681 B2 | 3/2005 | Laboureau et al. | |
| 6,902,932 B2 | 6/2005 | Altman et al. | |
| 6,946,003 B1 * | 9/2005 | Wolowacz et al. | 623/23.72 |
| 6,966,918 B1 | 11/2005 | Schuldt-Hempe et al. | |
| 6,971,252 B2 | 12/2005 | Therin et al. | |
| 7,021,086 B2 | 4/2006 | Ory et al. | |
| 7,025,063 B2 * | 4/2006 | Snitkin et al. | 128/885 |
| 7,115,388 B2 | 10/2006 | Tsubouchi | |
| 7,156,858 B2 | 1/2007 | Schuldt-Hempe et al. | |
| 7,166,570 B2 | 1/2007 | Hunter et al. | |
| 7,285,637 B2 | 10/2007 | Armato et al. | |
| 7,293,433 B2 | 11/2007 | McMurray | |
| 7,331,199 B2 | 2/2008 | Ory et al. | |
| 7,338,531 B2 | 3/2008 | Ellis et al. | |
| 7,341,601 B2 | 3/2008 | Eisermann et al. | |
| 7,476,249 B2 | 1/2009 | Frank | |
| 7,614,258 B2 * | 11/2009 | Cherok et al. | 66/192 |
| 7,824,701 B2 | 11/2010 | Binette et al. | |
| 7,828,855 B2 | 11/2010 | Ellis et al. | |
| 7,842,780 B2 | 11/2010 | Kaplan et al. | |
| 7,875,074 B2 | 1/2011 | Chen et al. | |
| 7,900,484 B2 | 3/2011 | Cherok et al. | |
| 8,007,531 B2 | 8/2011 | Frank | |
| 8,177,834 B2 * | 5/2012 | Carlson et al. | 623/1.51 |
| 8,197,542 B2 | 6/2012 | Becker | |
| 8,202,317 B2 | 6/2012 | Becker | |
| 8,226,715 B2 * | 7/2012 | Hwang et al. | 623/13.14 |
| 2002/0156437 A1 | 10/2002 | McDevitt et al. | |
| 2003/0044155 A1 * | 3/2003 | Maiden | 385/137 |
| 2003/0061839 A1 * | 4/2003 | Kost | 66/192 |
| 2003/0087433 A1 | 5/2003 | Tsubouchi et al. | |
| 2003/0106346 A1 * | 6/2003 | Matsumoto | 66/195 |
| 2003/0106347 A1 * | 6/2003 | Kost | 66/195 |
| 2003/0165548 A1 | 9/2003 | Tsubouchi et al. | |
| 2003/0183978 A1 | 10/2003 | Asakura | |
| 2003/0228815 A1 * | 12/2003 | Bhatnagar et al. | 442/164 |
| 2004/0005363 A1 | 1/2004 | Tsukada et al. | |
| 2004/0029478 A1 | 2/2004 | Planck et al. | |
| 2004/0170827 A1 | 9/2004 | Crighton | |
| 2004/0211225 A1 * | 10/2004 | Dickerson | 66/142 |
| 2004/0219630 A1 | 11/2004 | Tsubouchi | |
| 2004/0224406 A1 | 11/2004 | Altman et al. | |
| 2005/0089552 A1 | 4/2005 | Altman et al. | |
| 2005/0240261 A1 * | 10/2005 | Rakos et al. | 623/1.51 |
| 2005/0260706 A1 | 11/2005 | Kaplan et al. | |
| 2005/0288797 A1 * | 12/2005 | Howland | 623/23.74 |
| 2006/0009835 A1 * | 1/2006 | Osborne et al. | 623/1.13 |
| 2006/0013950 A1 * | 1/2006 | Porter et al. | 427/171 |
| 2007/0088434 A1 | 4/2007 | Frank et al. | |
| 2007/0207186 A1 * | 9/2007 | Scanlon et al. | 424/424 |
| 2008/0038236 A1 | 2/2008 | Gimble et al. | |
| 2008/0131509 A1 | 6/2008 | Hossainy et al. | |
| 2008/0176960 A1 | 7/2008 | Tsukada et al. | |
| 2008/0200086 A1 * | 8/2008 | Porter et al. | 442/189 |
| 2008/0206302 A1 | 8/2008 | Sittinger et al. | |
| 2008/0228028 A1 * | 9/2008 | Carlson et al. | 600/36 |
| 2008/0300683 A1 | 12/2008 | Altman et al. | |
| 2009/0024162 A1 | 1/2009 | Shalaby et al. | |
| 2009/0030454 A1 | 1/2009 | Knight et al. | |
| 2009/0214649 A1 | 8/2009 | Gazit et al. | |
| 2010/0023029 A1 | 1/2010 | Young et al. | |

(56) References Cited

U.S. PATENT DOCUMENTS

| | | |
|---|---|---|
| 2010/0145367 A1 | 6/2010 | Ratcliffe |
| 2010/0209405 A1 | 8/2010 | Altman et al. |
| 2010/0249924 A1 | 9/2010 | Powell et al. |
| 2010/0256756 A1 | 10/2010 | Altman et al. |
| 2011/0009960 A1 | 1/2011 | Altman et al. |
| 2011/0022171 A1 | 1/2011 | Richter et al. |
| 2011/0054604 A1 | 3/2011 | Becker et al. |
| 2011/0054605 A1 | 3/2011 | Becker et al. |
| 2011/0106249 A1 | 5/2011 | Becker et al. |
| 2011/0167602 A1 | 7/2011 | Altman et al. |
| 2011/0171453 A1 | 7/2011 | Altman et al. |
| 2011/0184227 A1 | 7/2011 | Altman et al. |
| 2011/0189773 A1 | 8/2011 | Altman et al. |
| 2011/0190795 A1 | 8/2011 | Hotter et al. |
| 2011/0224703 A1 | 9/2011 | Mortarino et al. |
| 2011/0257665 A1 | 10/2011 | Mortarino et al. |
| 2011/0257761 A1 | 10/2011 | Mortarino et al. |
| 2011/0282365 A1 | 11/2011 | Hadba et al. |
| 2011/0301717 A1 | 12/2011 | Becker |
| 2012/0053690 A1 | 3/2012 | Frank |
| 2012/0165957 A1 | 6/2012 | Everland et al. |
| 2012/0184974 A1 | 7/2012 | Becker |
| 2012/0226352 A1 | 9/2012 | Becker |
| 2012/0244143 A1 | 9/2012 | Lo et al. |

FOREIGN PATENT DOCUMENTS

| | | |
|---|---|---|
| EP | 0677297 | 10/1995 |
| EP | 0889156 A1 | 12/1996 |
| EP | 1241178 | 9/2002 |
| EP | 2016956 | 1/2009 |
| EP | 2068766 | 10/2011 |
| JP | H06-245989 | 9/1994 |
| WO | 95-25550 | 9/1995 |
| WO | 00-57812 | 10/2000 |
| WO | WO 00/72782 | 12/2000 |
| WO | WO 02/29141 | 4/2002 |
| WO | WO 2004/062697 | 7/2004 |
| WO | WO 2005/123114 | 12/2005 |
| WO | 2006102477 | 9/2006 |
| WO | WO 2009/023615 | 2/2009 |
| WO | WO 2010/074827 | 7/2010 |
| WO | WO 2010/141133 | 12/2010 |

OTHER PUBLICATIONS

Cappello et al., In-situ self-assembling protein polymer gel systems for administration, delivery, and release of drugs, USA *Journal of controlled release: official journal of the Controlled Release Society* (Apr. 30, 1998), 53(1-3):105-17, San Diego, CA 92121.

Horan et al., In vitro degradation of silk fibroin, USA *Biomaterials* (Jun. 2005), 26(17):3385-93.

Horan, et al., Biological and biomechanical assessment of a long-term bioresorbable silk-derived surgical mesh in an abdominal body wall defect model, *Hernia* (2009) 13(2):189-99.

Kardestuncer et al., RGD-tethered silk substrate stimulates the differentiation of human tendon cells, *Clinical Orthopaedics and Related Research* (2006), No. 448:pp. 234-239.

Kundu et al., Natural protective glue protein, sericin bioengineered by silkworms: Potential for biomedical and biotechnological applications, *Progress in Polymer Science* (2008) 33:998-1012.

Panilaitis et al., Macrophage responses to silk, *Biomaterials* (2003) 24(18):3079-3085.

Tamada, Y., Symposium Preprints, *The Society of Fiber Science and Technology* (1998) p. S-51.

Tsukada, Preparation and application of porous silk fibroin materials, *Journal of Applied Polymer Science* (1994).

Yanagisawa et al., Improving cell-adhesive properties of recombinant bombyx mori silk by incorporation of collagen or fibronectin derived peptides produced by transgenic silkworms, *Biomacromolecules* (2007), 8 (11):3487-3492.

Zhu et al., Preparation and Characterization of Regenerated Bombyx mori silk fibroin fiber containing recombinant cell-adhesive proteins; nonwoven fiber and monofilament, *Journal of Applied Polymer Science* (2008), vol. 109:2956-2963.

\* cited by examiner

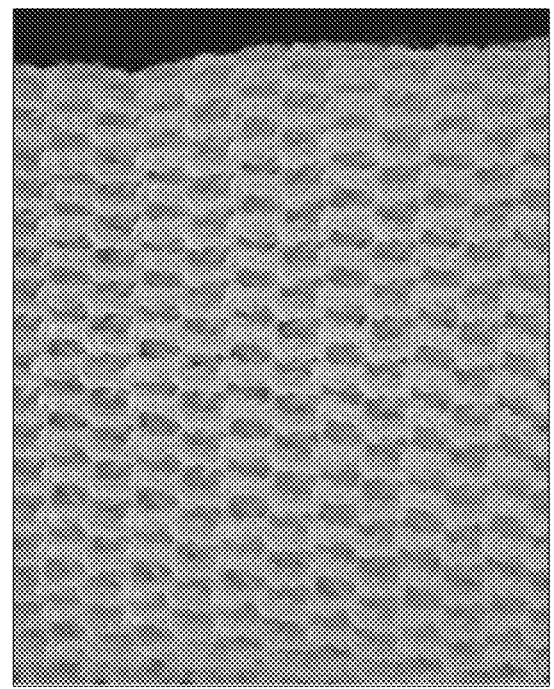
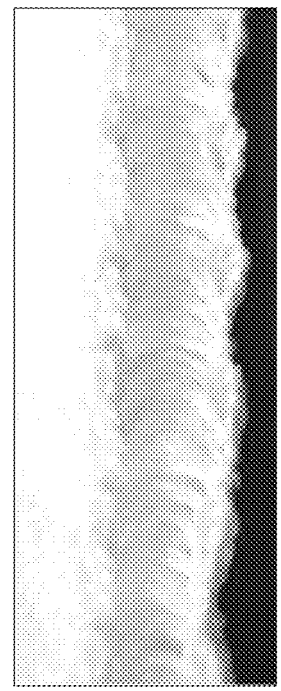
FIG. 14A
FIG. 14B

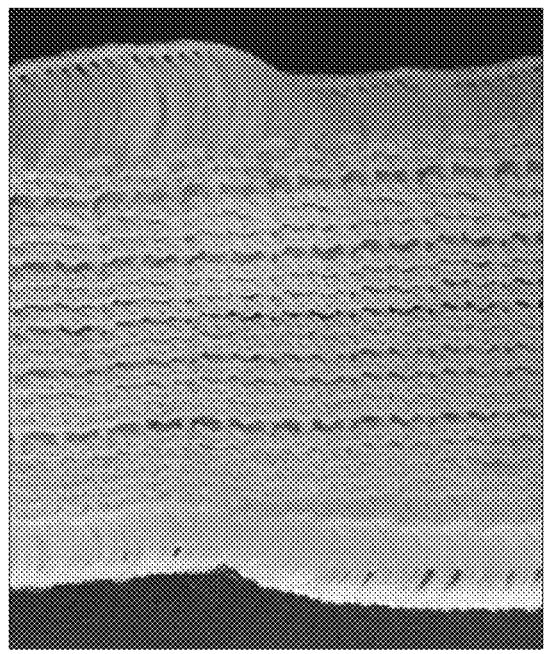

○    NODE AT CORNER OF PART

▱    WALES

▱    WEFTS

▱    CROSSES AT 45°

▱    CROSSES AT 45°

=== CROSS MEMBERS

WALES

WALES

OR

KNITTED SCAFFOLD WITH DIAGONAL YARN

CROSS-REFERENCE TO RELATED APPLICATIONS

This application is a continuation-in-part application which claims priority to U.S. utility patent application Ser. No. 12/680,404, filed Mar. 26, 2010, which is a national stage entry of PCT/US09/63717, filed Nov. 9, 2009, claiming priority to U.S. provisional patent application No. 61/122,520, filed Dec. 15, 2008, all of which applications are hereby expressly incorporated by reference herein in their entireties.

FIELD OF THE INVENTION

The present invention generally relates to a prosthetic device for tissue repair, and, more particularly, to a surgical silk mesh device employing a stable knit structure.

BACKGROUND OF THE INVENTION

Surgical mesh initially used for hernia and abdominal wall defects are now being used for other types of tissue repair, such as rotator cuff repair, pelvic floor dysfunction, and reconstructive or cosmetic surgeries. It is projected that in 2010, there will be more than 8 million hernia procedures, 800,000 rotator cuff repairs, 3 million pelvic prolapse repairs, 600,000 urinary incontinence repairs, and 1.5 million reconstructive or aesthetic plastic surgeries. Most of these procedures will likely employ implantable surgical mesh devices currently on the market, including: Bard Mesh (polypropylene) by C. R. Bard; Dexon (polyglycolic acid) by Synecture/US Surgical; Gore-Tex (polytetrafluoroethylene) by W. L. Gore; Prolene (polypropylene), Prolene Soft (polypropylene), Mersilene Mesh (polyester), Gynemesh (polypropylene), Vicryl Knitted Mesh (polyglactin 910), TVT (polypropylene) by Ethicon; Sparc tape (polypropylene) by American Medical Systems; and IVS tape (polypropylene) by TYCO Healthcare International.

Surgical mesh devices are typically biocompatible and may be formed from bioresorbable materials and/or non-bioresorbable materials. For example, polypropylene, polyester, and polytetrafluoroethylene (PTFE) are biocompatible and non-bioresorbable, while polyglactin 910 and polyglycolic acid are biocompatible and bioresorbable.

Though current surgical mesh devices may be formed from different materials, they have various similar physical and mechanical characteristics beneficial for tissue repair. However, despite the benefits provided by current surgical mesh devices, their use may be accompanied by a variety of complications. Such complications, for example, may include scar encapsulation and tissue erosion, persistent infection, pain, and difficulties associated with revision surgery. In addition, the use of an absorbable material may result in reoccurrence due to rapid resorption of the implant material and loss of strength.

Although polypropylene monofilament may be a highly regarded material for surgical mesh devices, polypropylene mesh devices can induce intense scar formations and create a chronic foreign body reaction with the formation of a fibrous capsule, even years after implantation. Minor complaints of seromas, discomfort, and decreased wall mobility are frequent and observed in about half of the patients implanted with polypropylene mesh devices. Moreover, polypropylene generally cannot be placed next to the bowel due to the propensity of adhesion formation.

Although the use of multifilament polyester may improve conformity with the abdominal wall, it is also associated with a variety of disadvantages. For example, higher incidences of infection, enterocutaneous fistula formation, and small bowel obstruction have been reported with the use of multifilament polyester compared to other materials. Indeed, the small interstices of the multifilament yarn make it more susceptible to the occurrence of infection, and thus multifilament polyester is not commonly used within the United States.

The use of polytetrafluoroethylene (PTFE) may be advantageous in minimizing adhesions to the bowel. However, the host tissue encapsulates the PTFE mesh, resulting in weak in-growth in the abdominal wall and weaker hernia repair. This material, though not a good mesh material on its own, has found its place as an adhesion barrier.

Absorbable materials, such as Vicryl and Dexon, used for hernia repair have the advantage of being placed in direct contact with the bowel without adhesion or fistula formation. A study has observed that Vicryl has comparable burst strength to nonabsorbable mesh at three weeks but is significantly weaker at twelve weeks due to a quick absorption rate. Meanwhile, the same study observed that Dexon has more in-growth at twelve weeks with less absorption of the mesh. The concern with absorbable meshes is that the rate of absorption is variable, possibly leading to hernia recurrence if the proper amount of new tissue is not there to withstand the physiologic stresses placed on the hernia defect.

A significant characteristic of a biomaterial is its porosity, because porosity is the main determinant for tissue reaction. Pore sizes of >500-600 μm permit in-growth of soft tissue; pore sizes of >200-300 μm favor neo-vascularisation and allow mono-morphological restitution of bony defects; pore sizes of <200 μm are considered to be almost watertight, hindering liquid circulation at physiological pressures; and pores of <100 μm only lead to in-growth of single cell types instead of building new tissues. Finally, a pore size of <10 μm hinders any in-growth and increases the chance of infection, sinus tract formation, and encapsulation of the mesh. Bacteria averaging 1 μm in size can hide in the small interstices of the mesh and proliferate while protected from neutrophilic granulocytes averaging 10-15 μm.

Other important physical characteristics for surgical mesh devices include thickness, burst strength, and material stiffness. The thickness of surgical mesh devices vary according to the particular repair procedure. For example, current surgical mesh device hernia, pelvic floor dysfunction, and reconstructive/cosmetic procedures range in thickness from approximately 0.635 mm to 1.1 mm. For rotator cuff repair, a thickness of 0.4 mm to 5 mm is typically employed.

Intra-abdominal pressures of 10-16 N, with a mean distension of 11-32% results in the need for a surgical mesh with a burst strength that can resist the stress of the inner abdomen before healthy tissue comes into being.

Material stiffness is an important mechanical characteristic for surgical mesh, especially when used for pelvic floor dysfunction, because material stiffness has been associated with the likelihood of tissue erosion. Surgical mesh devices formed from TVT, IVS, Mersilene, Prolene, Gynemesh, Sparc tape, for example, currently have an ultimate tensile strength (UTS) that exceeds the forces exerted by intra-abdominal pressures of 10-16 N. With the low force in the abdomen, the initial stiffness of the material is an important consideration. Moreover, the stiffness may exhibit non-linear behavior most likely due to changes in the fabric structure, e.g., unraveling of the knit, weave, etc. A surgical mesh device of lesser stiffness may help reduce tissue erosion and may conform to the contours of the body more effectively.

SUMMARY OF THE INVENTION

In view of the disadvantages of current surgical mesh devices, there continues to be a need for a surgical mesh that is biocompatible and absorbable, has the ability to withstand the physiological stresses placed on the host collagen, and minimizes tissue erosion, fistulas, or adhesions. Thus, embodiments according to aspects of the present invention provide a biocompatible surgical silk mesh prosthetic device for use in soft and hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh device degrades at a rate which allows for a smooth transfer of mechanical properties to the new tissue from the silk scaffold. According to a particular aspect of the present invention, embodiments employ a knit pattern, referred to as a "node-lock" design. The "node-lock" design substantially prevents unraveling and preserves the stability of the mesh device, especially when the mesh device is cut.

In a particular embodiment, a prosthetic device includes a knitted mesh including at least two yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes.

In an example of this embodiment, the first yarn and the second yarn are formed from different materials. In another example of this embodiment, the first yarn and the second yarn have different diameters. In further embodiments, wherein the first yarn and the second yarn have different elastic properties. In yet a further example of this embodiment, the at least two yarns are formed from silk.

In another example of this embodiment, a first length of the first yarn extends between the two nodes and a second length of the second yarn extends between the two nodes, the first length being greater than the second length. For instance, the first yarn forms an intermediate loop between the two nodes and the second yarn does not form a corresponding intermediate loop between the two nodes. The first length of the first yarn is greater than the second length of the second yarn.

In yet another example of this embodiment, the first yarn is included in a first set of yarns and the second yarn is included in a second set of yarns, the first set of yarns being applied in a first wale direction, each of the first set of yarns forming a first series of loops at each of a plurality of courses for the knitted mesh, the second set of yarns being applied in a second wale direction, the second wale direction being opposite from the first wale direction, each of the second set of yarns forming a second series of loops at every other of the plurality of courses for the knitted mesh, the first set of yarns interlacing with the second set of yarns at the every other course to define the nodes for the knitted mesh, the second set of yarns having a greater tension than the first set of yarns, the difference in tension substantially preventing the knitted mesh from unraveling at the nodes.

In a further example of this embodiment, the first yarn is included in a first set of yarns and the second yarn is included in a second set of yarns, the first set of yarns and the second set of yarns being alternately applied in a wale direction to form staggered loops, the first set of yarns interlacing with the second set of yarns to define the nodes for the knitted mesh, the alternating application of the first set of yarns and the second set of yarns causing the first set of yarns to have different tensions relative to the second set of yarns at the nodes, the difference in tension substantially preventing the knitted mesh from unraveling at the nodes.

In yet a further example of this embodiment, the first yarn is included in a first set of yarns and the second yarn is included in a second set of yarns, the first set of yarns forming a series of jersey loops along each of a first set of courses for a knitted mesh, the second set of yarns forming a second series of alternating tucked loops and jersey loops along each of a second set of courses for the knitted mesh, the second set of courses alternating with the first set of courses, the second set of yarns having a greater tension than the first set of yarns, the tucked loops of the second set of yarns engaging the jersey loops of the first set of yarns to define nodes for the knitted mesh, the tucked loops substantially preventing the knitted mesh from unraveling at the nodes.

In another particular embodiment, a method for making a knitted mesh for a prosthetic device, includes: applying a first set of yarns in a first wale direction on a single needle bed machine, each of the first set of yarns forming a first series of loops at each of a plurality of courses for a knitted mesh; applying a second set of yarns in a second wale direction on the single needle bed machine, the second wale direction being opposite from the first wale direction, each of the second set of yarns forming a second series of loops at every other of the plurality of courses for the knitted mesh; and applying a third set of yarns in every predetermined number of courses for the knitted mesh, the application of the third set of yarns defining openings in the knitted mesh, wherein the first set of yarns interlaces with the second set of yarns at the every other course to define nodes for the knitted mesh, and the second set of yarns has a greater tension than the first set of yarns, the difference in tension substantially preventing the knitted mesh from unraveling at the nodes.

In yet another embodiment, a method for making a knitted mesh for a prosthetic device, includes: applying a first set of yarns to a first needle bed of a double needle bed machine in a wale direction; applying a second set of yarns to a second needle bed of the double needle bed machine in a wale direction; and applying a third set of yarns in every predetermined number of courses for the knitted mesh, the application of the third set of yarns defining openings in the knitted mesh, wherein the first set of yarns and the second set of yarns are alternately applied to form staggered loops at the first needle bed and the second needle bed, respectively, and the first set of yarns interlaces with the second set of yarns to define nodes for the knitted mesh, the alternating application of the first set of yarns and the second set of yarns causing the first set of yarns to have a different tension relative to the second set of yarns at the nodes, the difference in tension substantially preventing the knitted mesh from unraveling at the nodes.

In a further particular embodiment, a method for making a knitted mesh for a prosthetic device, includes: forming, on a flat needle bed machine, a first series of jersey loops along each of a first set of courses for a knitted mesh; and forming, on the flat needle bed machine, a second series of alternating tucked loops and jersey loops along each of a second set of courses for the knitted mesh, the second set of courses alternating with the first set of courses; wherein the second set of courses has a greater tension than the first set of courses, and the tucked loops along the second set of courses engage the jersey loops of the first set of courses and substantially prevents the knitted mesh from unraveling at the tucked loops. In an example of this embodiment, a continuous yarn forms the first set of courses and the second set of courses. In another example of this embodiment, the first set of courses and the second set of courses are formed by different yarns. In yet another example of this embodiment, the first set of courses and the second set of courses are formed by different yarns having different diameters.

A further embodiment of the present invention can comprise a knitted scaffold comprising at least two silk yarns in a knit direction and a yarn member diagonal to the knit direction. The diagonal yarn member can provide load bearing support. The diagonal yarn member can be at a 45 degree to 60 degree angle from the knit direction. The diagonal yarn member can be in a single plane or in two planes. Yet a further embodiment of the present invention comprises a method of making a knitted silk scaffold having at least two yarns in a knit direction that resists collapse when opposing forces are applied at an angle from the knit direction by placing a yarn member diagonally to the knit direction of the scaffold and the yarn member can be diagonally at a 45 degree to 60 degree angle to the knit direction and the yarn member can be placed diagonally in a single plane or in two planes. The scaffold can be knitted on a single needle bed machine or on a double needle bed machine. As well the scaffold can be knitted using two or three needle bars.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 2 illustrates an example mesh produced on a double needle bed warp knitting machine according to aspects of the present invention. Thus.

FIG. 14A illustrates an example of a three-dimensional mesh with the same technical front and technical back according to aspects of the present invention.

FIG. 14B illustrates the 5.36 mm thickness of the example three-dimensional mesh of FIG. 14A.

FIG. 15A illustrates the technical front of an example three-dimensional mesh fabric according to aspects of the present invention.

FIG. 15B illustrates the technical back of the example three-dimensional mesh fabric of FIG. 15A.

FIG. 21C illustrates an explanted specimen 94 days post implantation as shown in FIG. 21B.

DETAILED DESCRIPTION

Figure 1B:
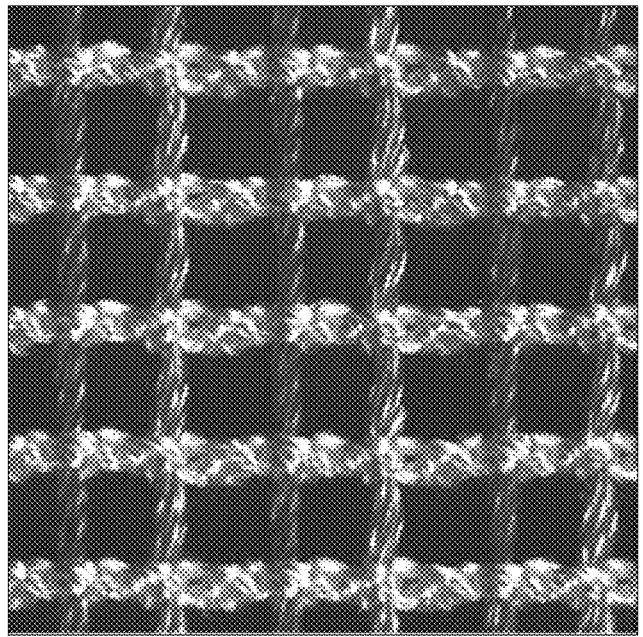
FIG. 1B illustrates the technical front of the example mesh illustrated in FIG. 1A.

Embodiments according to aspects of the present invention provide a biocompatible surgical silk mesh device for use in soft or hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh bioresorbs at a rate which allows for a smooth transfer of mechanical properties to the new tissue from the silk scaffold. Furthermore, embodiments employ a knit pattern that substantially prevents unraveling, especially when the mesh device is cut. In particular, embodiments may preserve the stability of the mesh device by employing a knit pattern that takes advantage of variations in tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as intermesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places the at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

In general, node-lock designs according to aspects of the present invention employ at least two yarns under different tensions, where a higher tension yarn restricts a lower tension yarn at the mesh nodes. To achieve variations in tension between yarns, other node-lock designs may vary the yarn diameter, the yarn materials, the yarn elastic properties, and/or the knit pattern. For example, the knit pattern described previously applies yarns in varying lengths to create slack in some yarns so that they experience less tension. Because the lower tension yarn is restricted by the higher tension yarn, node-lock designs substantially prevent unraveling of the mesh when the mesh is cut. As such, the embodiments allow the mesh device to be cut to any shape or size while maintaining the stability of the mesh device. In addition, node-lock designs provide a stability that makes it easy to pass the mesh device through a cannula for laparoscopic or arthroscopic surgeries without damaging the material.

Although the node-lock design may employ a variety of polymer materials, a mesh device using silk according to aspects of the present invention can bioresorb at a rate sufficient to allow tissue in-growth while slowly transferring the load-bearing responsibility to the native tissue. Particular embodiments may be formed from *Bombyx mori* silkworm silk fibroin. The raw silk fibers have a natural globular protein coating known as sericin, which may have antigenic properties and must be depleted before implantation. Accordingly, the yarn is taken through a depletion process. The depletion of sericin is further described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk material used in the device embodiments contains substantially no sensitizing agents, in so far as can be measured or predicted with standardized biomaterials test methods.

Figure 22:
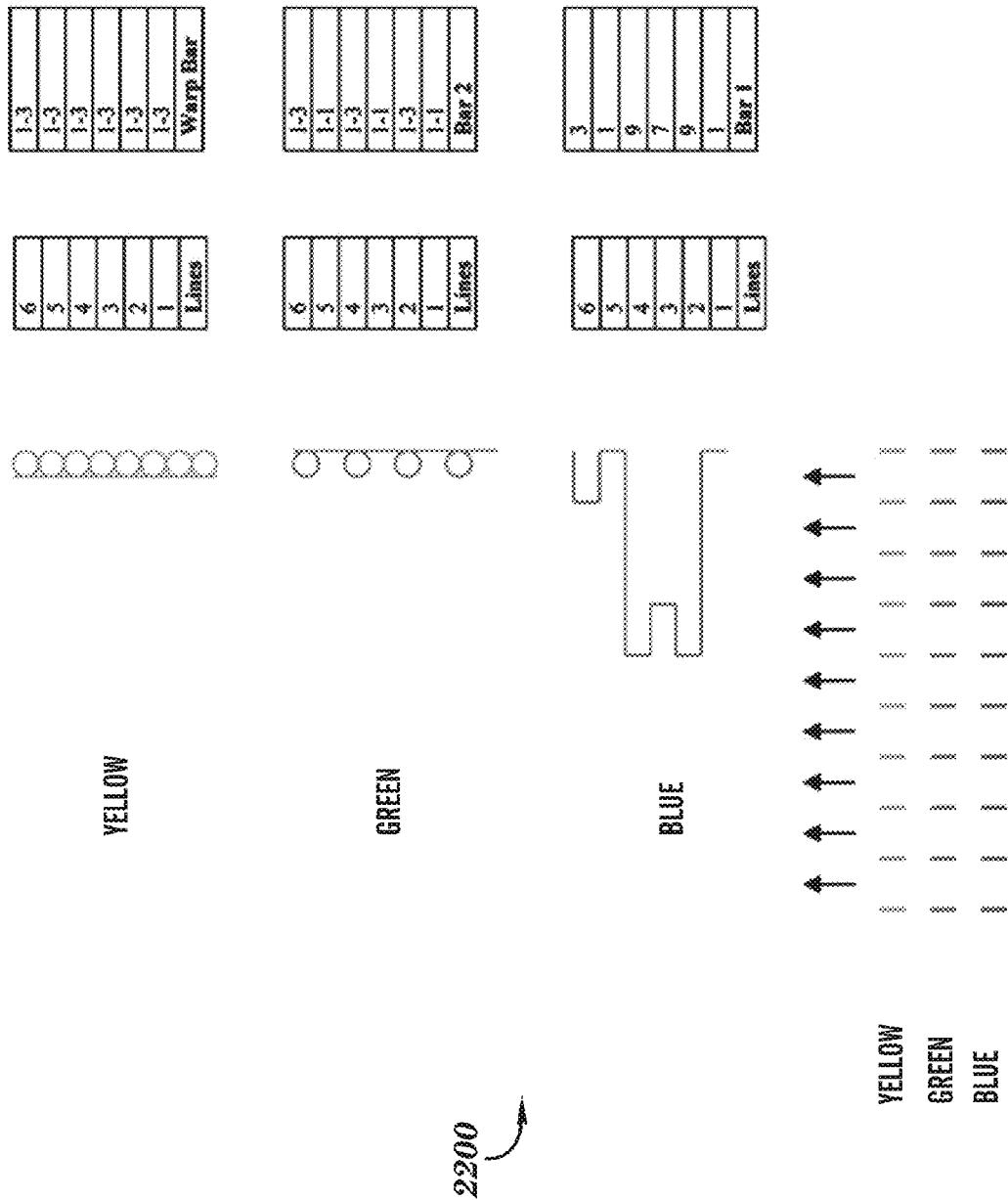
FIG. 22 illustrates an example pattern layout for a single needle bed mesh according to aspects of the present invention.

A surgical mesh device according to aspects of the present invention may be created on a single needle bed Comez Acotronic/600-F or a Comez 410 ACO by the use of three movements as shown in the pattern layout 2200 in FIG. 22: two movements in the wale direction, the vertical direction within the fabric, and one in the course direction, the horizontal direction of the fabric. The movements in the wale direction go in opposing directions; a first yarn moving in one direction loops every course while the second yarn moving in the opposite direction loops every other course. The yarns follow a repeated pattern of 3-1 and 1-1/1-3 on a 20 gauge knitting machine, using only half of the needles available on the needle bed. The interlacing of the loops within the fabric allow for one yarn to become under more tension than the other under stress, locking it around the less tensioned yarn; keeping the fabric from unraveling when cut. The other movement within the fabric occurs in every few courses creating the openings in the mesh. These yarns follow a pattern of 1-9/9-7/7-9/9-1/1-3/3-1. These yarns create tension within the fabric when under stress, locking the yarns in the fabric; preventing the fabric from unraveling.

Figure 26:
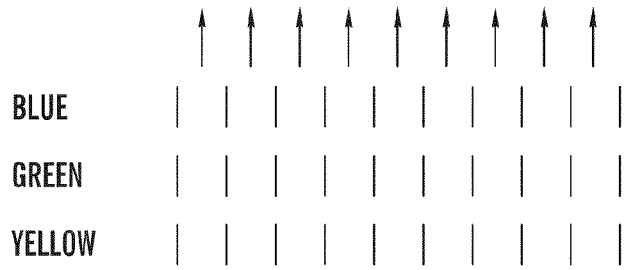
FIG. 26 illustrates an example pattern layout of the double needle bed mesh according to aspects of the present invention.

A surgical mesh device according to aspects of the present invention may be created on a double needle bed Comez DNB/EL-800-8B knitting machine by the use of three movements as shown in the pattern layout 2600 in FIG. 26: two movements in the wale direction and one in the course direction. The two movements in the wale direction occur on separate needle beds with alternate yarns; loops that occur in every course movement are staggered within the repeat. The yarns follow a repeated pattern of 3-1/1-1/1-3/3-3 and 1-1/1-3/3-3/3-1. The third movement happens with the yarn that traverses the width of the fabric. The yarn follows the pattern 9-9/9-7/7-9/9-7/7-9/9-1/1-1/1-3/3-1/1-3-3/1-1. This fabric is also made at half gauge on a 20 gauge knitting machine and prevents unraveling due to the tension created between the yarns when stressed. The repeat the yarn follows within the pattern is illustrated in FIG. 26.

Figure 23:
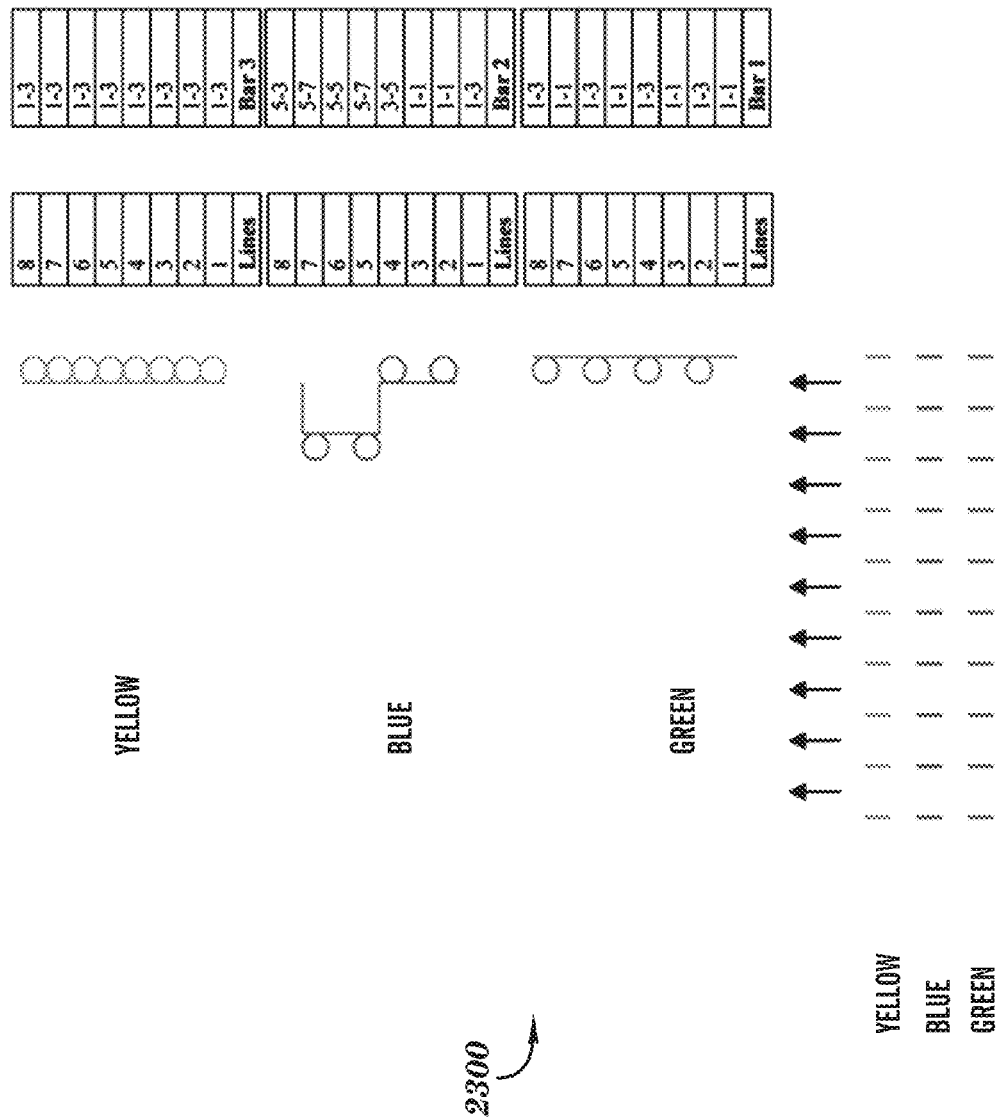
FIG. 23 illustrates an example pattern layout for a single needle bed mesh according to aspects of the present invention.
Figure 24:
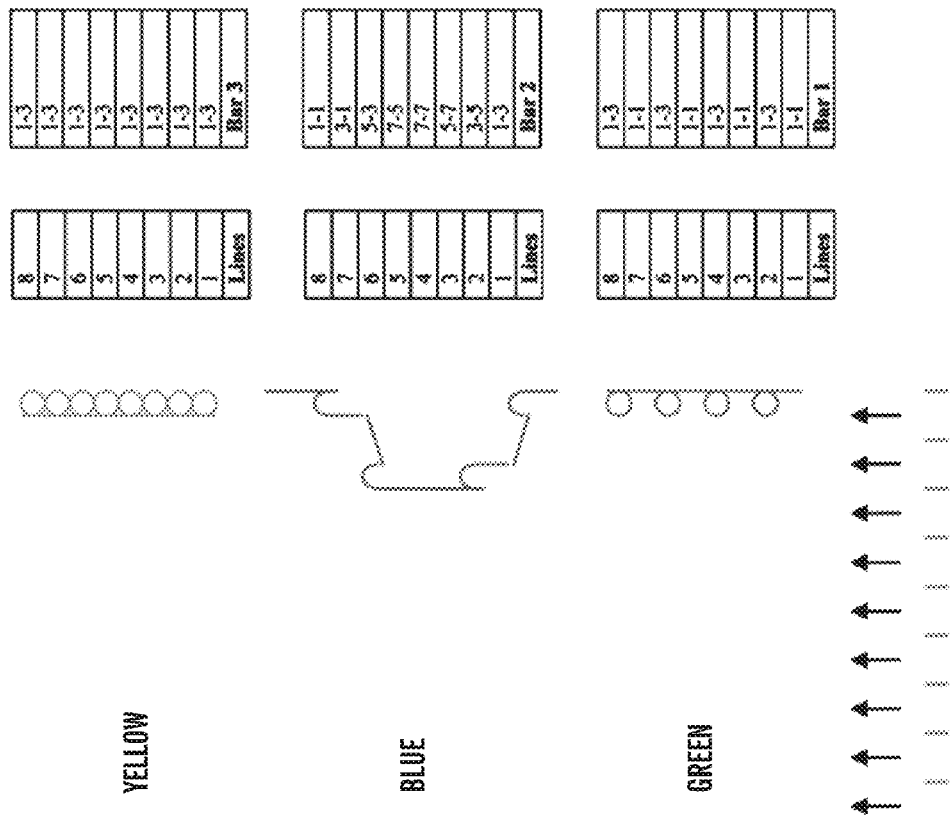
FIG. 24 illustrates an example pattern layout for a single needle bed mesh according to aspects of the present invention.
Figure 25:
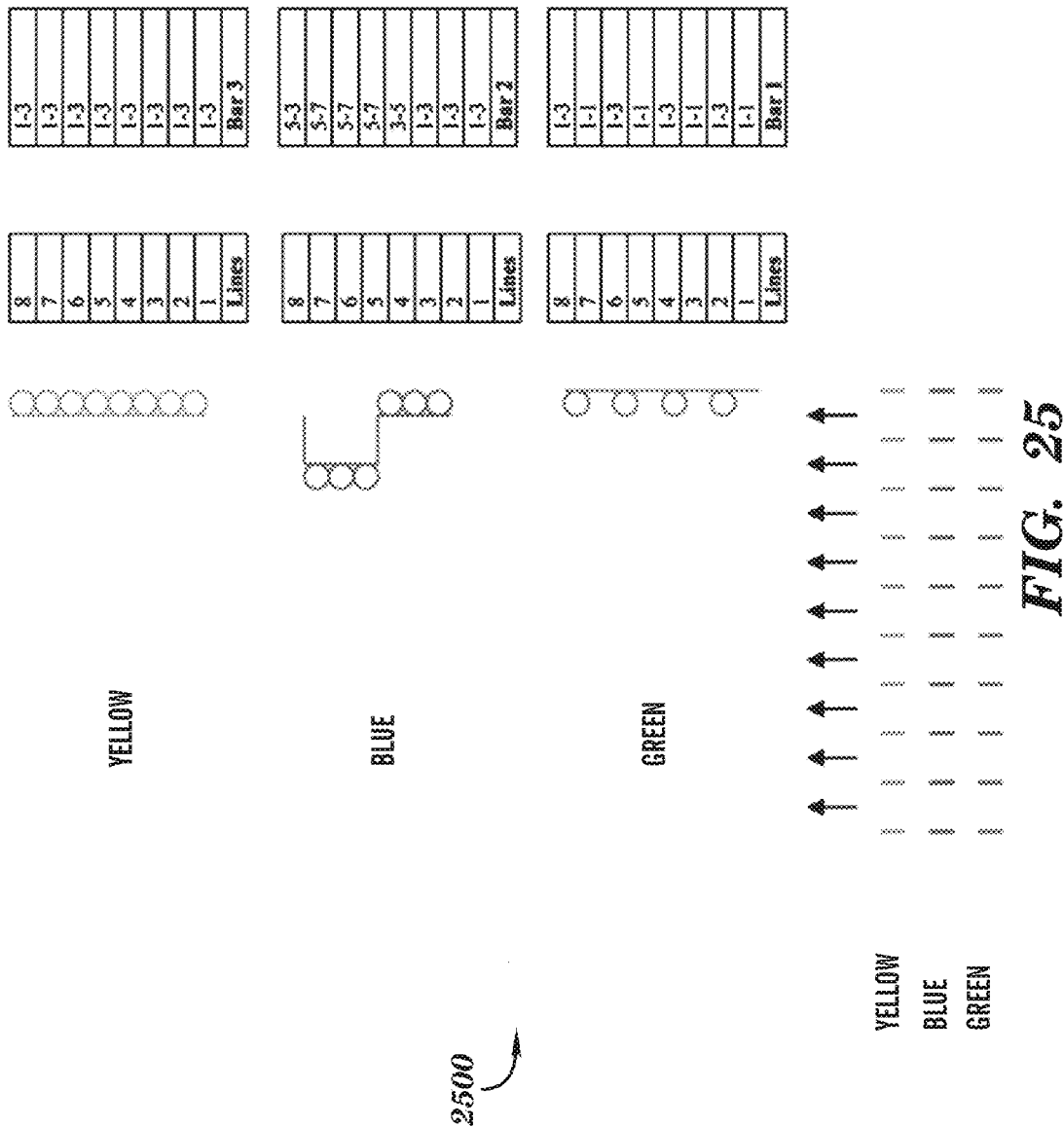
FIG. 25 illustrates an example pattern layout for the single needle bed mesh according to aspects of the present invention.

According to the pattern layouts 2300, 2400, and 2500 illustrated in FIGS. 23, 24 and 25, respectively, variations of the surgical mesh pattern are demonstrated for the Single Needle Bed including knitting with an added warp bar in place of using a weft bar insertion. These variations include knitting with the node lock yarns while moving it perpendicularly to one or more wales. These variations may include, but are not limited to, knitting either an open or closed chain stitch in either all or alternating courses. Utilizing a third warp bar, as opposed to a weft bar insertion can also be applied to the double needle warp knitting machine.

Figure 27:
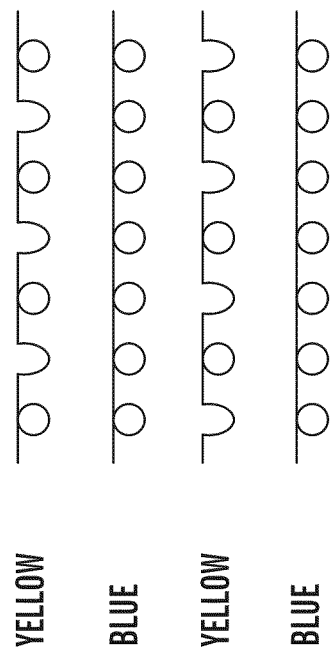
FIG. 27 illustrates an example pattern layout for the double needle bed weft knitting machine according to aspects of the present invention.

A surgical mesh device according to aspects of the present invention may be formed on the Shima Seiki flat needle bed machine as shown in the pattern layout 2700 in FIG. 27. This knit includes a continuous yarn or at least two different yarn sizes, one of which could be, though not limited to a different material. The knitted mesh would be formed by a regular jersey knit on the first row with loops formed by either a continuous yarn or a yarn of a certain yarn size, while the loops in the second row are formed by tucked loops that occur alternately with jersey knit loops of the same continuous yarn or with a yarn of a different size. The mesh would be shaped during knitting by use of increasing or decreasing stitches; a fashioning technique.

In embodiments employing silk yarn, the silk yarn may be twisted from yarn made by 20-22 denier raw silk fibers approximately 40 to 60 μm in diameter. Preferably, raw silk fibers ranging from 10 to 30 denier may be employed; however any fiber diameters that will allow the device to provide sufficient strength to the intended area are acceptable. Advantageously, a constant yarn size may maximize the uniformity of the surgical mesh mechanical properties, e.g. stiffness, elongation, etc., physical and/or biological properties. However, the yarn size may be varied in sections of the surgical mesh in order to achieve different mechanical, physical and/or biological characteristics in the preferred surgical mesh locations. Factors that may influence the size of the yarn include, but are not limited to: ultimate tensile strength (UTS); yield strength, i.e. the point at which yarn is permanently deformed; percent elongation; fatigue and dynamic laxity (creep); bioresorption rate; and transfer of cell/nutrients into and out of the mesh. The knit pattern layouts 2200, 2300, 2400, 2500, and 2600 illustrated in FIGS. 22-26, respectively, may be knitted to any width limited by the knitting machine width and could be knitted with any of the gauges available with the various crochet machine or warp knitting machine. TABLE 2 outlines the fabric widths that may be achieved using different numbers of needles on different gauge machines. It is understood that the dimensions in TABLE 1 are approximate due to the shrink factor which depends on stitch design, stitch density, and yarn size used.

TABLE 1

| Gauge | Needle Count | Knitting Width |
| --- | --- | --- |
| 48 | 2-5,656 | 0.53-2,997.68 mm |
| 24 | 2-2,826 | 1.06-2,995.56 mm |
| 20 | 2-2,358 | 1.27-2,994.66 mm |
| 18 | 2-2,123 | 1.41-2,993.43 mm |
| 16 | 2-1,882 | 1.59-2,992.38 mm |
| 14 | 2-1,653 | 1.81-2,991.93 mm |
| 12 | 2-1,411 | 2.12-2,991.32 mm |
| 10 | 2-1,177 | 2.54-2,989.58 mm |
| 5 | 2-586 | 5.08-2,976.88 mm |

Embodiments of a prosthetic device according to the present invention may be knitted on a fine gauge crochet knitting machine. A non-limiting list of crochet machines capable of manufacturing the surgical mesh according to aspects of the present invention are provided by: Changde Textile Machinery Co., Ltd.; Gomez; China Textile Machinery Co., Ltd.; Huibang Machine; Jakkob Muller A G; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Embodiments of a prosthetic device according to the present invention may be knitted on a fine gauge warp knitting machine. A non-limiting list of warp knitting machines capable of manufacturing the surgical mesh according to aspects of the present invention are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of a prosthetic device according to the present invention may be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger; Machinery; Fujian Hongqi; G & P Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

Figure 1A:
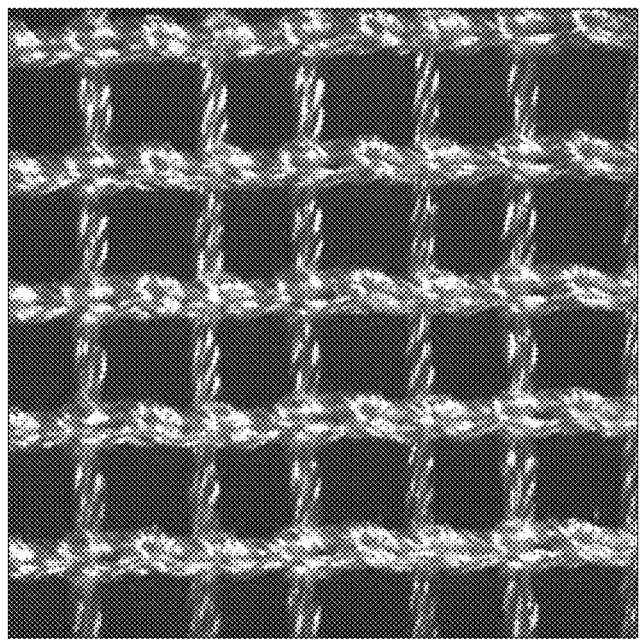
FIG. 1A illustrates the technical back of an example mesh produced on a single needle bed warp knitting machine according to aspects of the present invention.

FIGS. 1-20 illustrate example meshes produced according to aspects of the present invention. Referring to FIGS. 1A and B, an example mesh 100 is produced on a single needle bed warp knitting machine according to aspects of the present invention. FIG. 1A shows the technical back 100A of the mesh 100, and FIG. 1B shows the technical front 100B of the mesh 100.

Figure 2A:
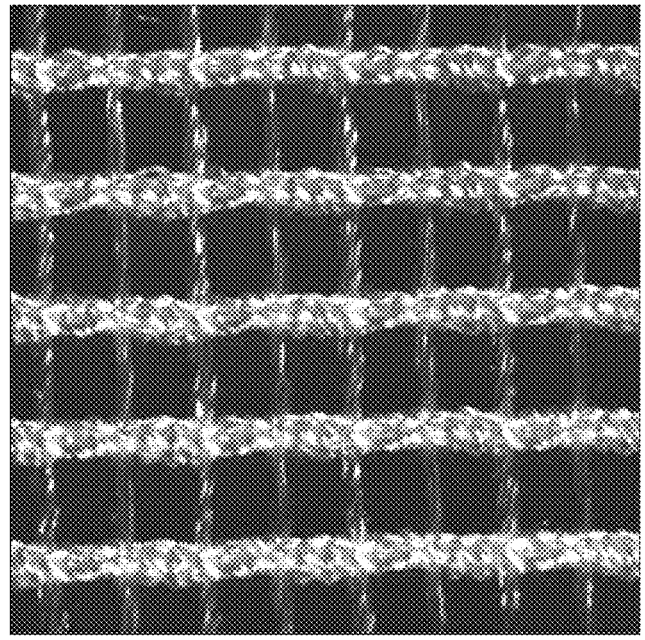
FIG. 2A shows the technical front 200A of the mesh 200 embodiment of the present invention.
Figure 2B:
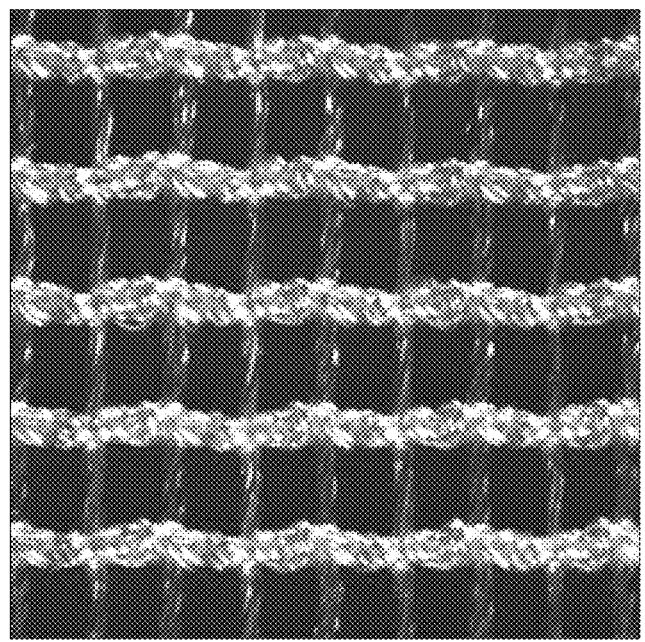
FIG. 2B shows the technical back 200B of the mesh 200 embodiment of the present invention.

Referring to FIGS. 2A and B, an example mesh 200 is produced on a double needle bed warp knitting machine according to aspects of the present invention. FIG. 2A shows the technical front 200A of the mesh 200, and FIG. 2B shows the technical back 200B of the mesh 200.

Figure 3:
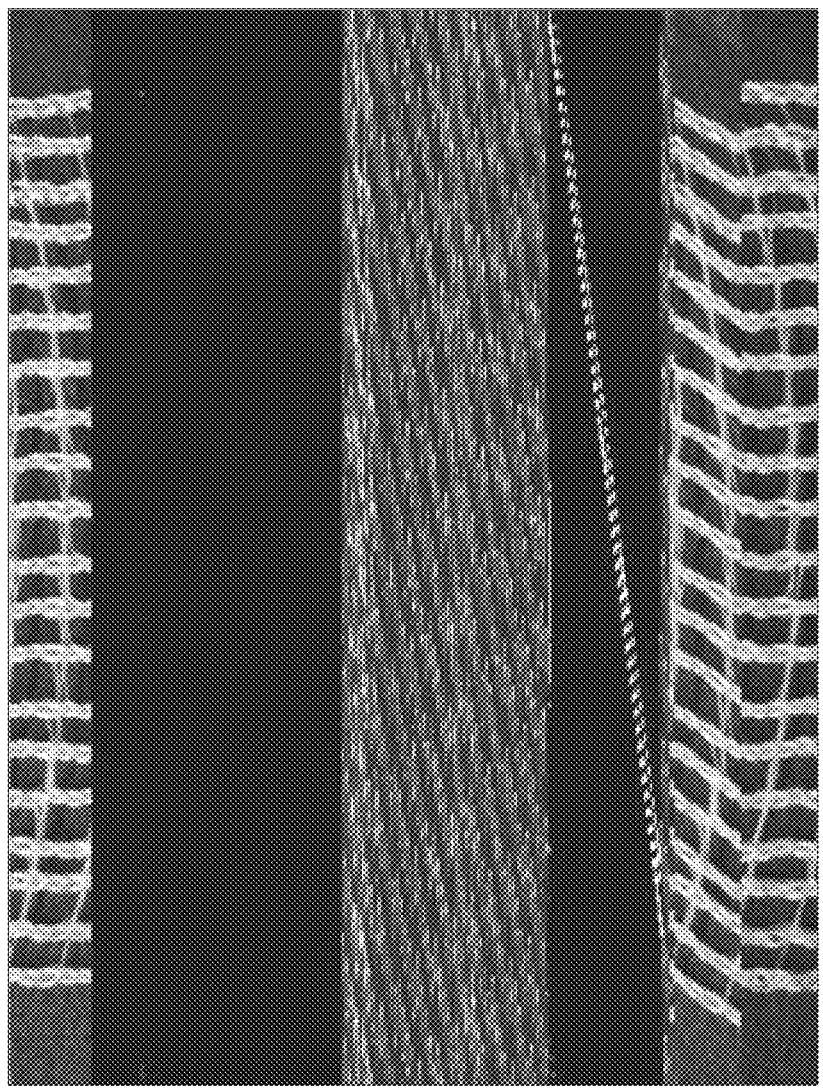
FIG. 3 illustrates an example mesh produced with single filament silk yarn according to aspects of the present invention.

FIG. 3 illustrates an example mesh 300 produced with single filament silk yarn according to aspects of the present invention.

Figure 4:
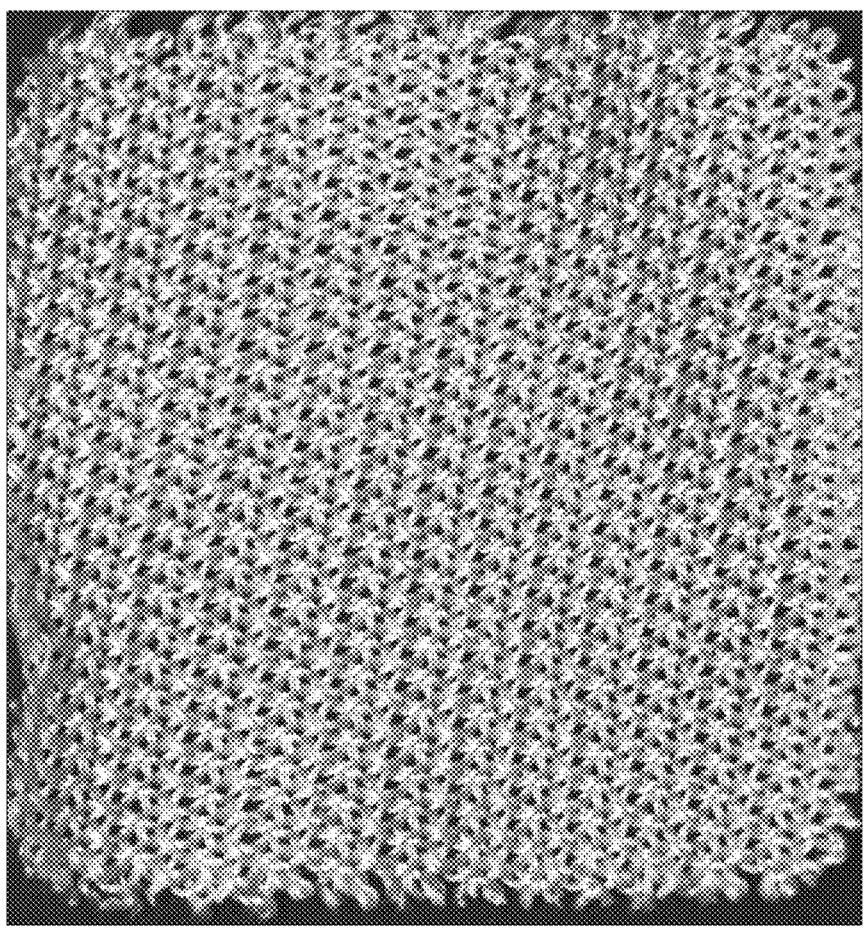
FIG. 4 illustrates an example mesh produced on a single needle bed warp knitting machine according to aspects of the present invention.

FIG. 4 shows an example mesh 400 produced on a single needle bed warp knitting machine according to aspects of the present invention.

Figure 5B:
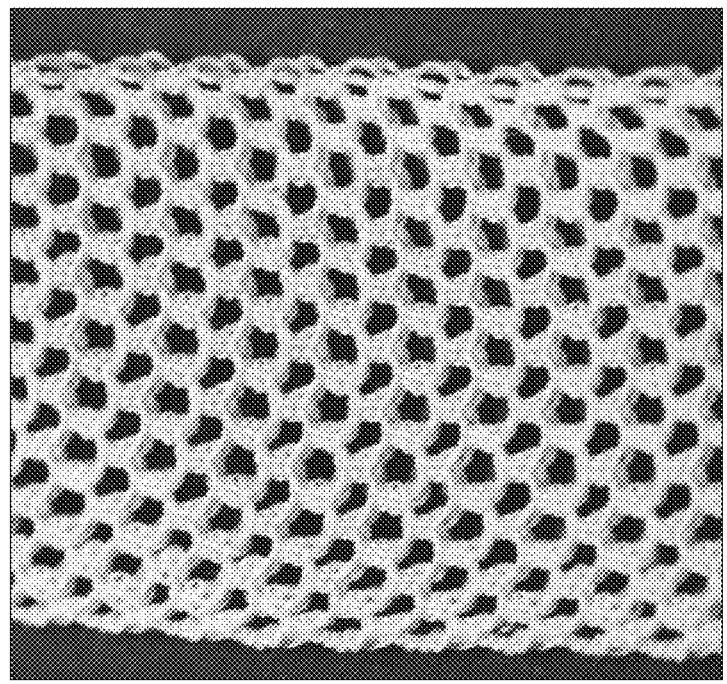
FIG. 5B illustrates an example mesh produced on a double needle bed warp knitting machine, the example mesh having a hexagonal pore according to aspects of the present invention.
Figure 5A:
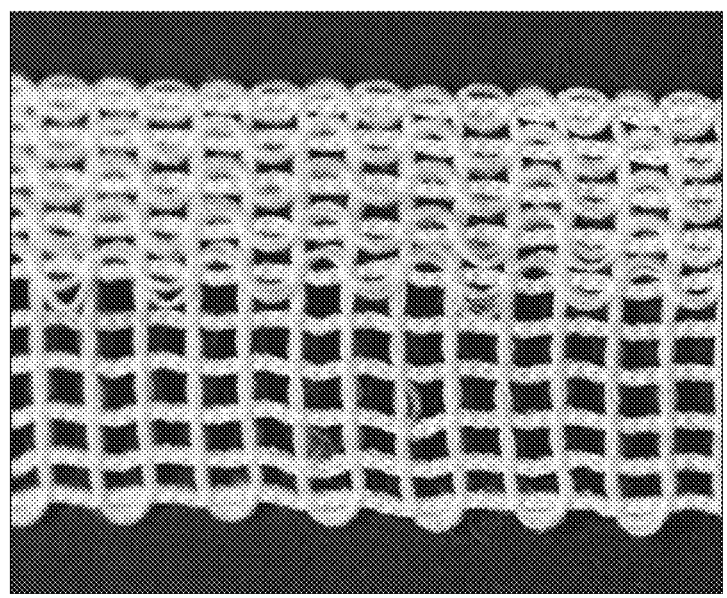
FIG. 5A illustrates an example mesh produced on a double needle bed warp knitting machine, the example mesh having a parallelepiped pore with a section demonstrating a plush design according to aspects of the present invention.

FIG. 5A illustrates an example mesh 500A produced on a double needle bed warp knitting machine. The mesh 500A has a parallelepiped pore with a section demonstrating a plush design according to aspects of the present invention. Meanwhile, FIG. 5B illustrates an example mesh 500B produced on a double needle bed warp knitting machine. The example mesh 500B has a hexagonal pore according to aspects of the present invention.

Figure 6B:
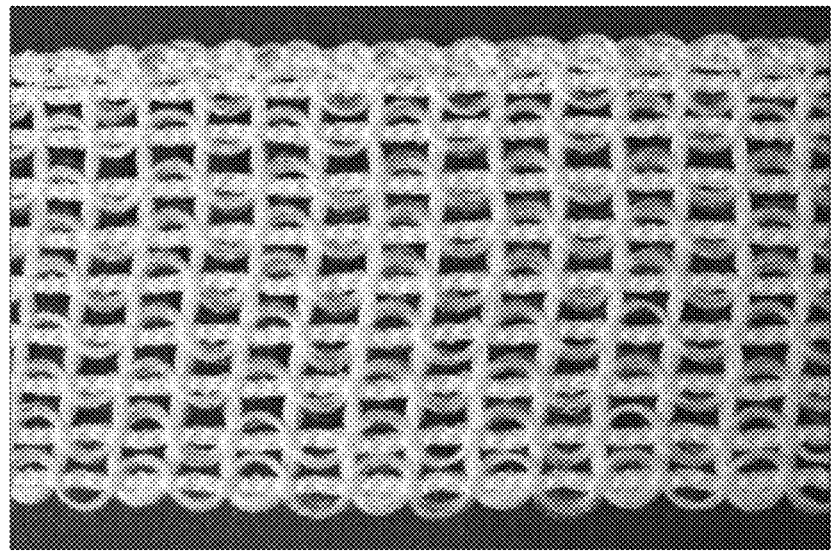
FIG. 6 illustrates example narrow mesh fabrics of varying stitch densities incorporating a plush variation according to aspects of the present invention. Thus, FIGS. 6A and B illustrate example narrow mesh fabrics 600A and 600B according to aspects of the present invention.
Figure 6A:
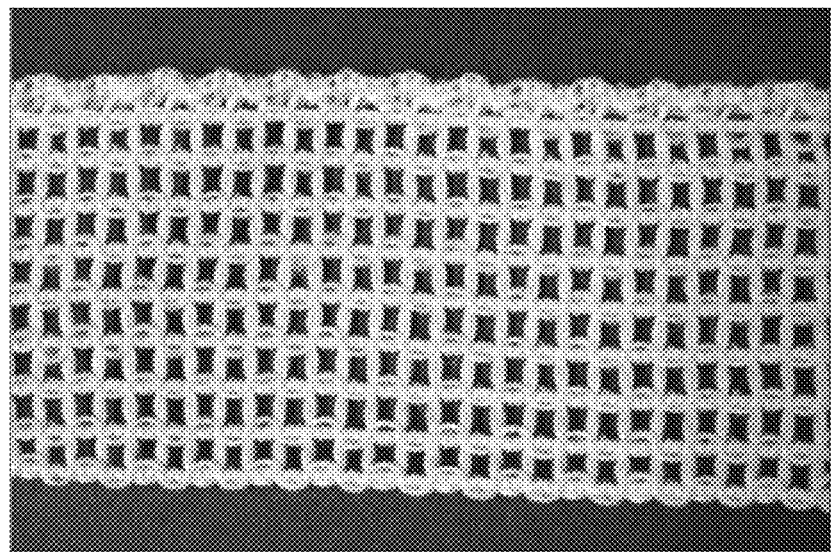

FIGS. 6A and B illustrate example narrow mesh fabrics 600A and 600B according to aspects of the present invention. The mesh fabrics 600A and 600B have varying stitch densities incorporating a plush variation.

Figure 7:
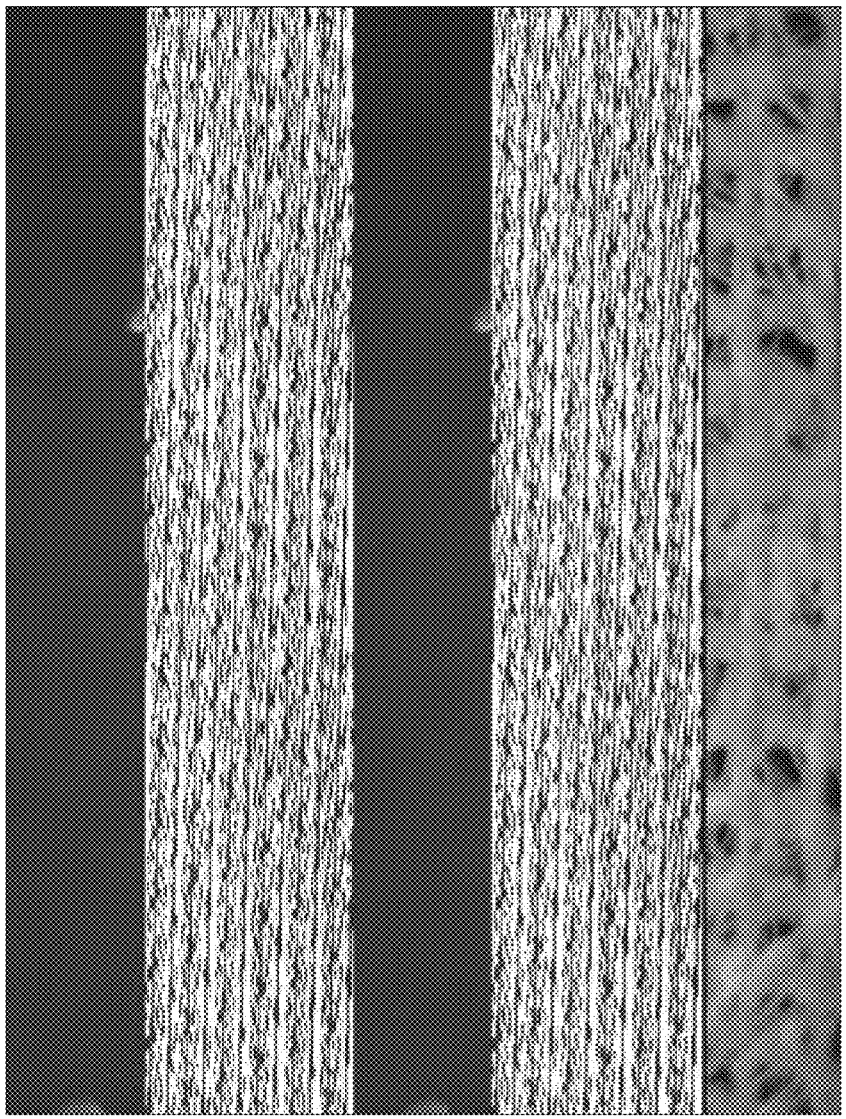
FIG. 7 illustrates an example mesh incorporating loop pile according to aspects of the present invention.
Figure 8:
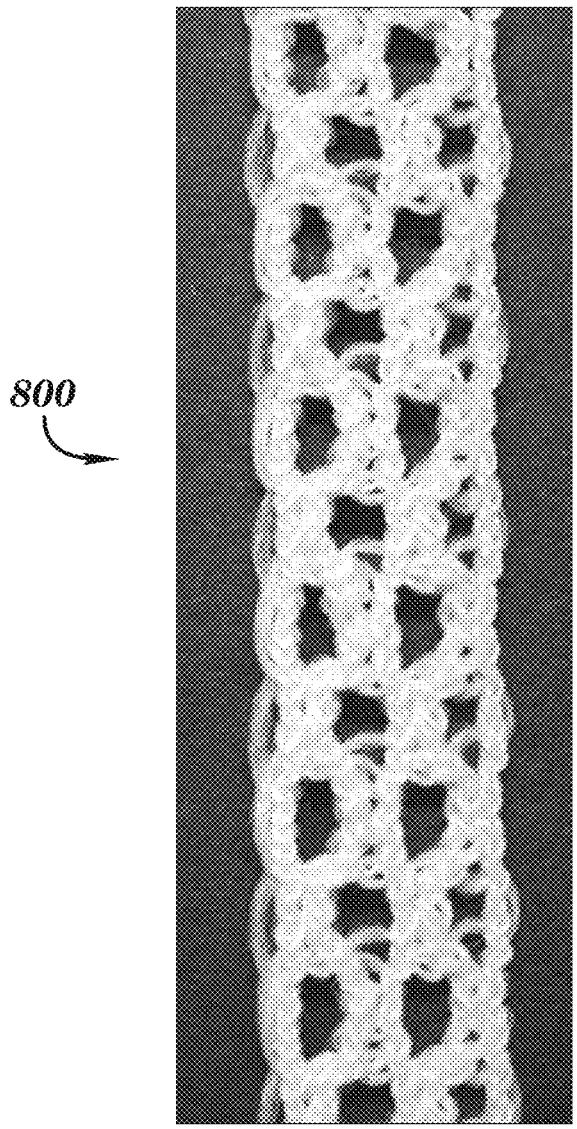
FIG. 8 illustrates an example narrow mesh fabric with pore design achieved through variation in the yarn feed rate according to aspects of the present invention.

Referring to FIG. 7, an example mesh 700 incorporates loop pile according to aspects of the present invention. FIG. 8 illustrates an example narrow mesh fabric 800 with pore design achieved through variation in the yarn feed rate according to aspects of the present invention.

Figure 9B:
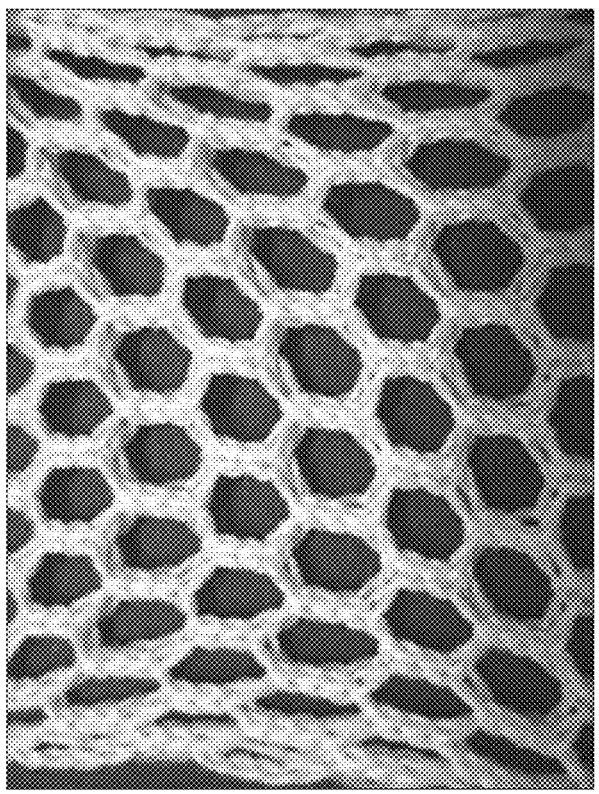
FIG. 9B illustrates an example opened mesh fabric with hexagonal shaped pores according to aspects of the present invention.
Figure 9A:
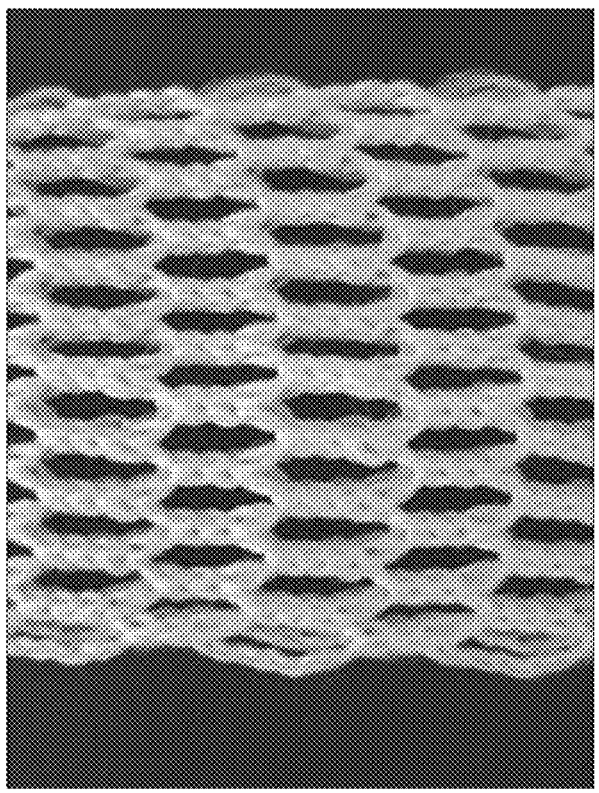
FIG. 9A illustrates an example collapsed mesh fabric with hexagonal shaped pores according to aspects of the present invention.

FIG. 9A illustrates an example collapsed mesh fabric 900A with hexagonal-shaped pores according to aspects of the present invention. Meanwhile, FIG. 9B illustrates an example opened mesh fabric 900B with hexagonal shaped pores according to aspects of the present invention.

Figure 10:
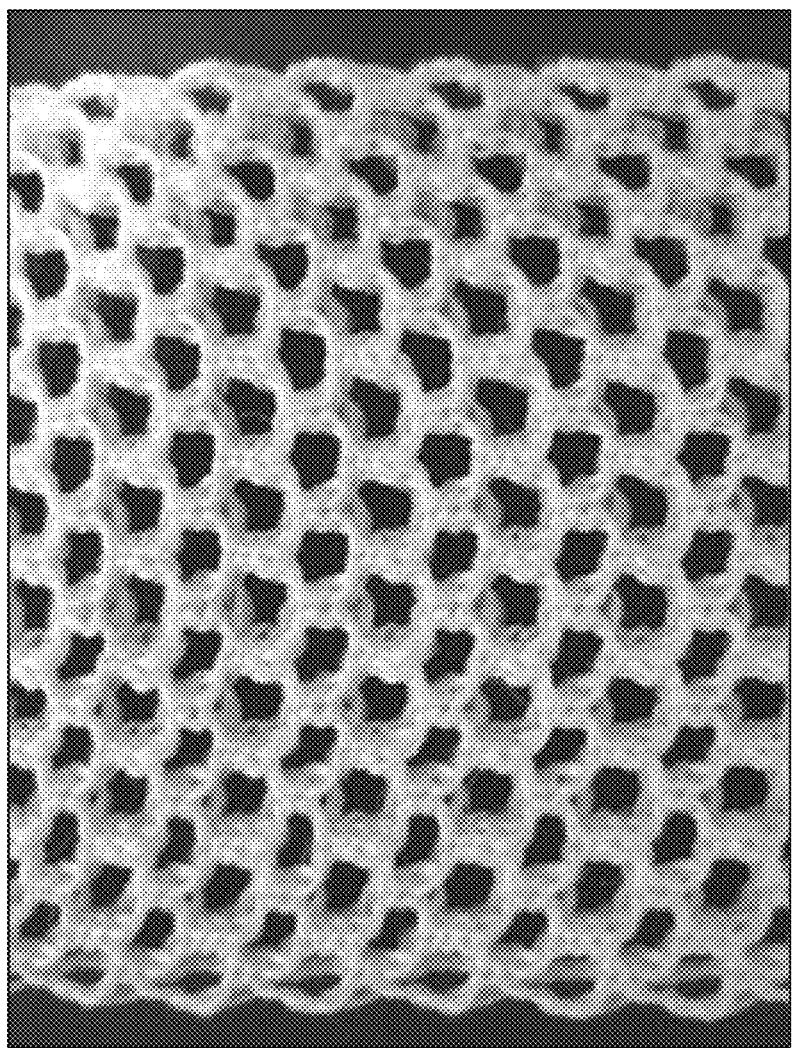
FIG. 10 illustrates an example of a stable, non-collapsible, hexagonal-shaped porous mesh fabric according to aspects of the present invention.

As shown in FIG. 10, an example of a stable, non-collapsible mesh fabric 1000 includes hexagonal-shaped pores according to aspects of the present invention.

Figure 11B:
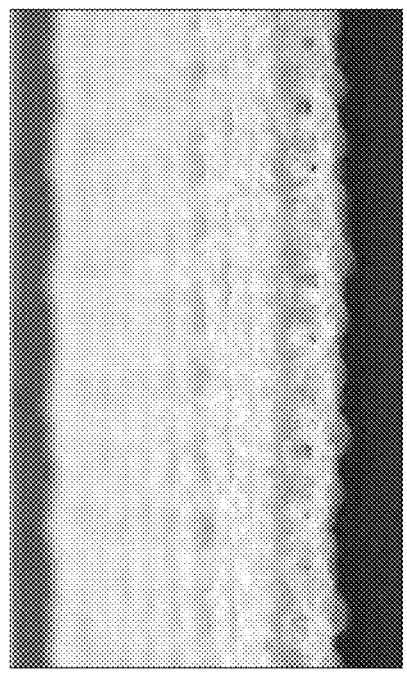
FIG. 11B illustrates the 2.55 mm thickness of the example three-dimensional mesh of FIG. 11A.
Figure 11A:
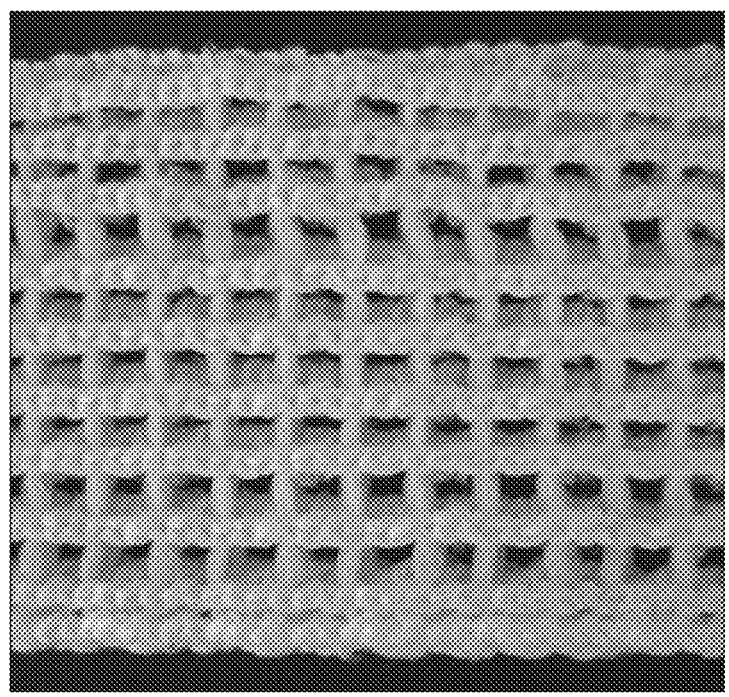
FIG. 11A illustrates an example of a three-dimensional mesh with the same technical front and technical back according to aspects of the present invention.
Figure 12:
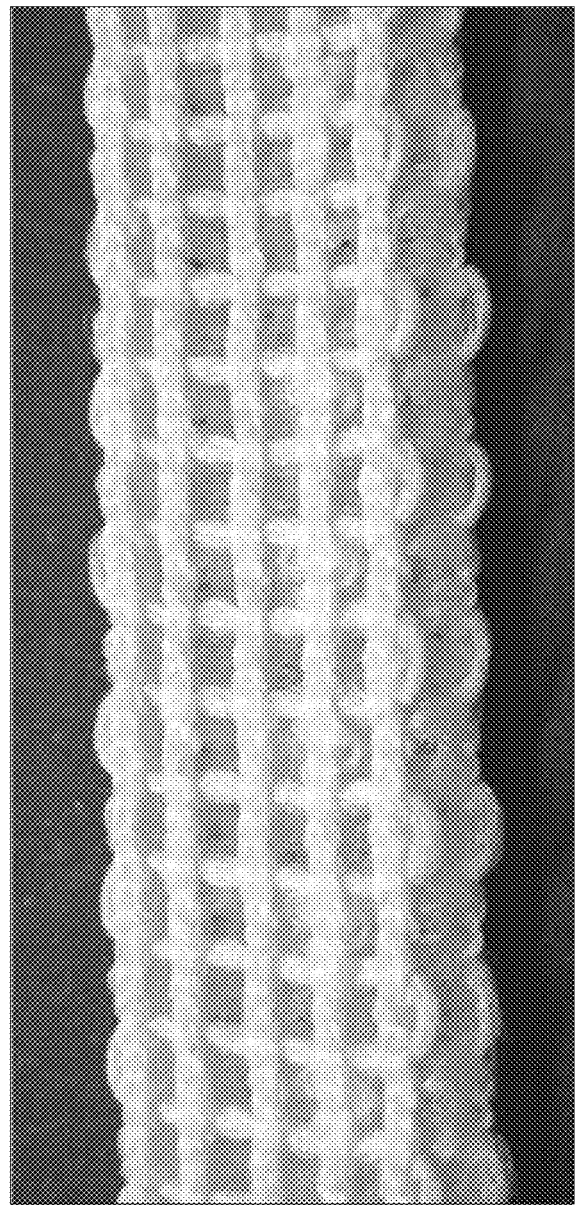
FIG. 12 illustrates an example of a three-dimensional mesh with a thickness of 3.28 mm according to aspects of the present invention.

FIG. 11A illustrate an example three-dimensional mesh 1100 with the same technical front and technical back according to aspects of the present invention. FIG. 11B illustrates the 2.55 mm thickness of the three-dimensional mesh 1100. FIG. 12 illustrates another example three-dimensional mesh 1200 with a thickness of 3.28 mm according to aspects of the present invention.

Figure 13A:
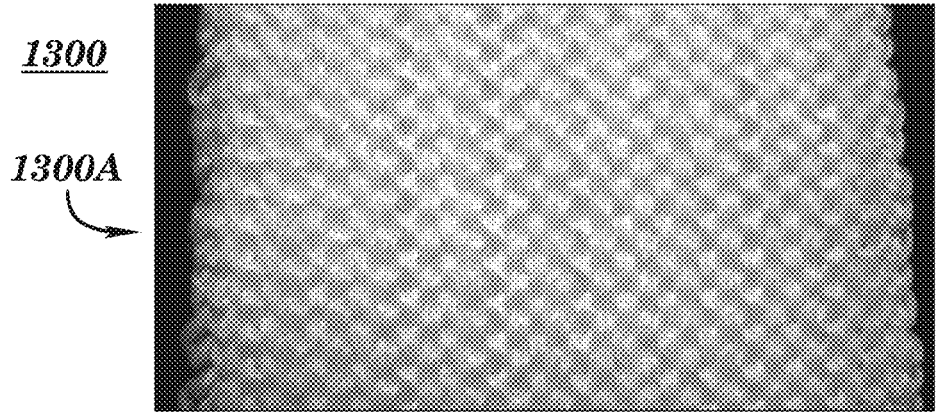
FIG. 13A illustrates the technical front of an example non-porous mesh according to aspects of the present invention.
Figure 13B:
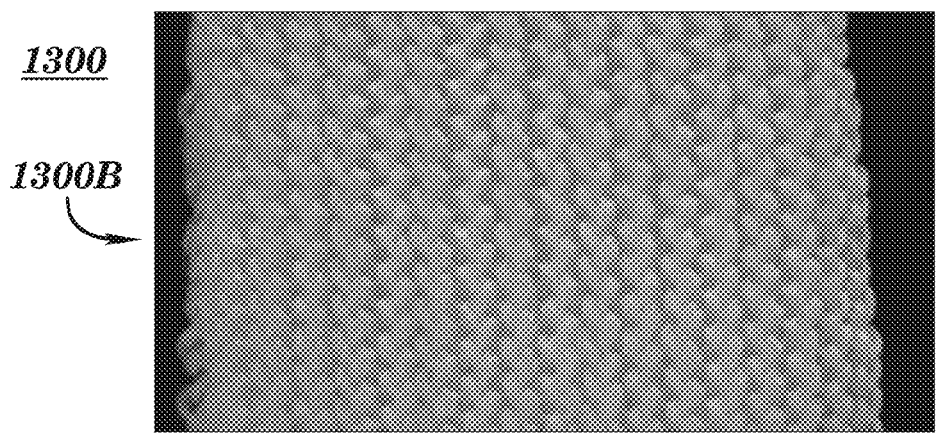
FIG. 13B illustrates the technical back of the example non-porous mesh of FIG. 13A.
Figure 13C:
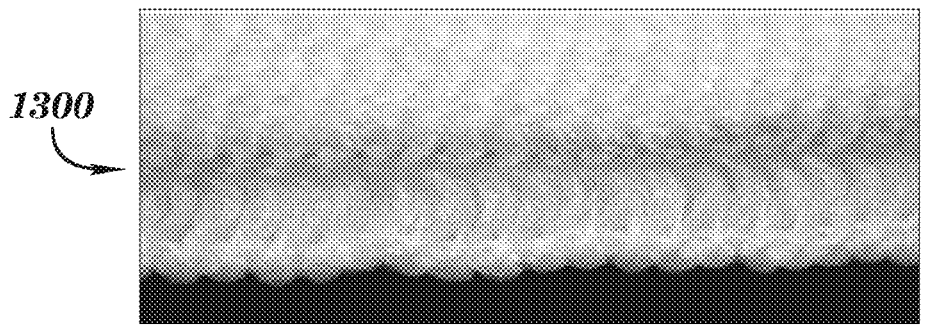
FIG. 13C illustrates the 5.87 mm thickness of the example non-porous mesh of FIG. 13A.
Figure 16:
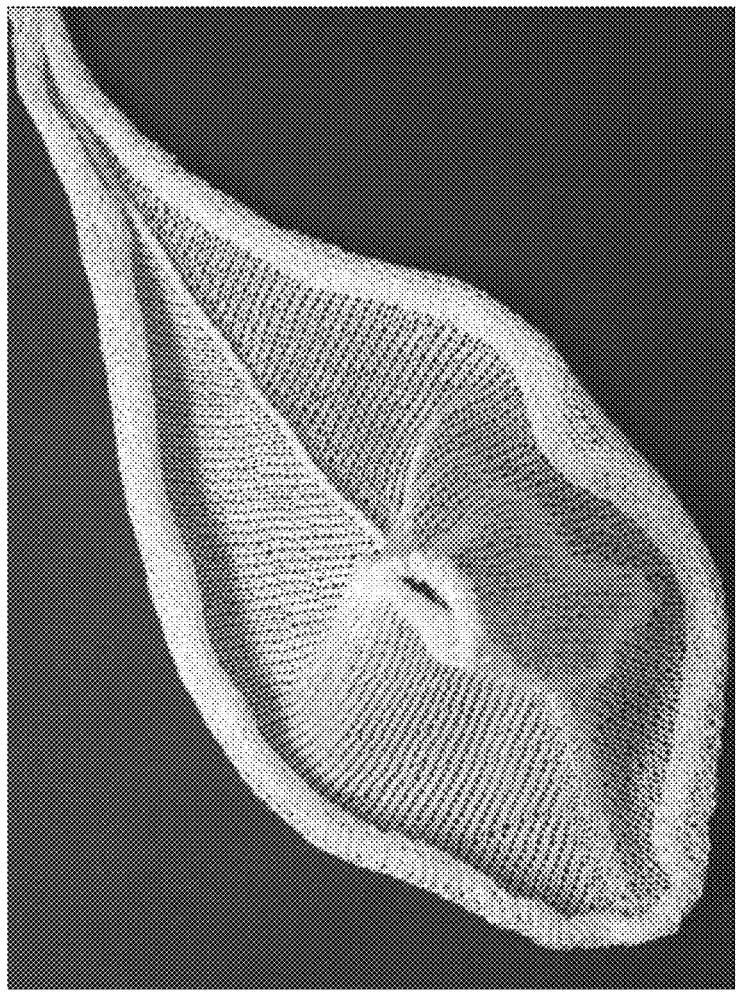
FIG. 16 illustrates an example mesh produced on a double needle bed weft knitting machine demonstrating shaping of the mesh for a breast support application according to aspects of the present invention.
Figure 17:
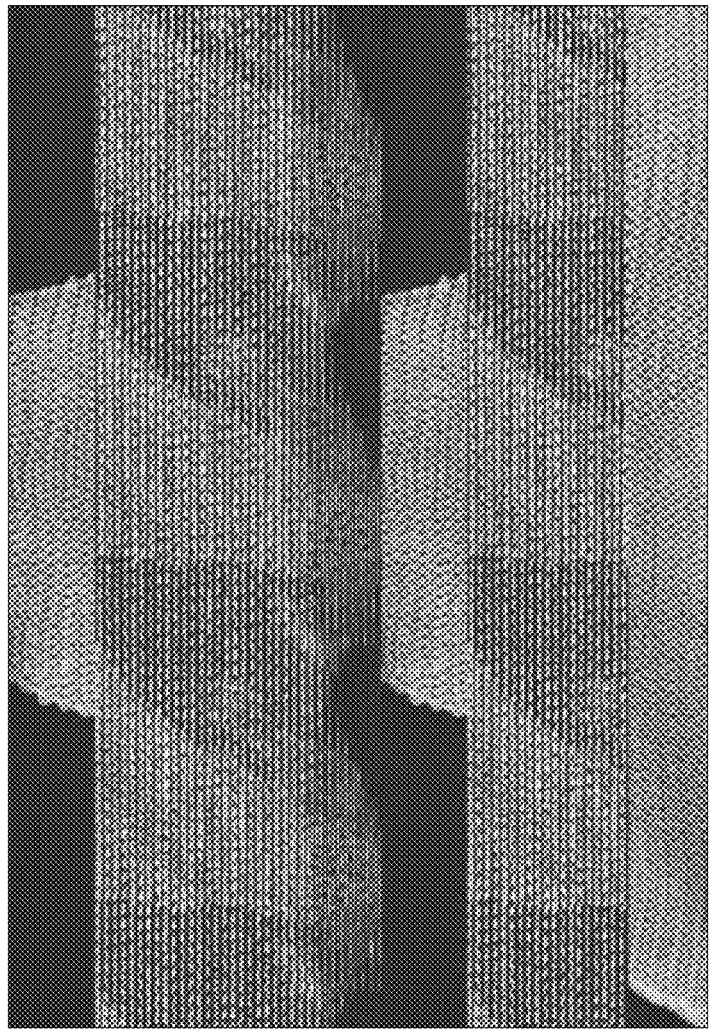
FIG. 17 illustrates another example mesh produced on a double needle bed weft knitting machine demonstrating shaping of the mesh for a breast support application according to aspects of the present invention.
Figure 18:
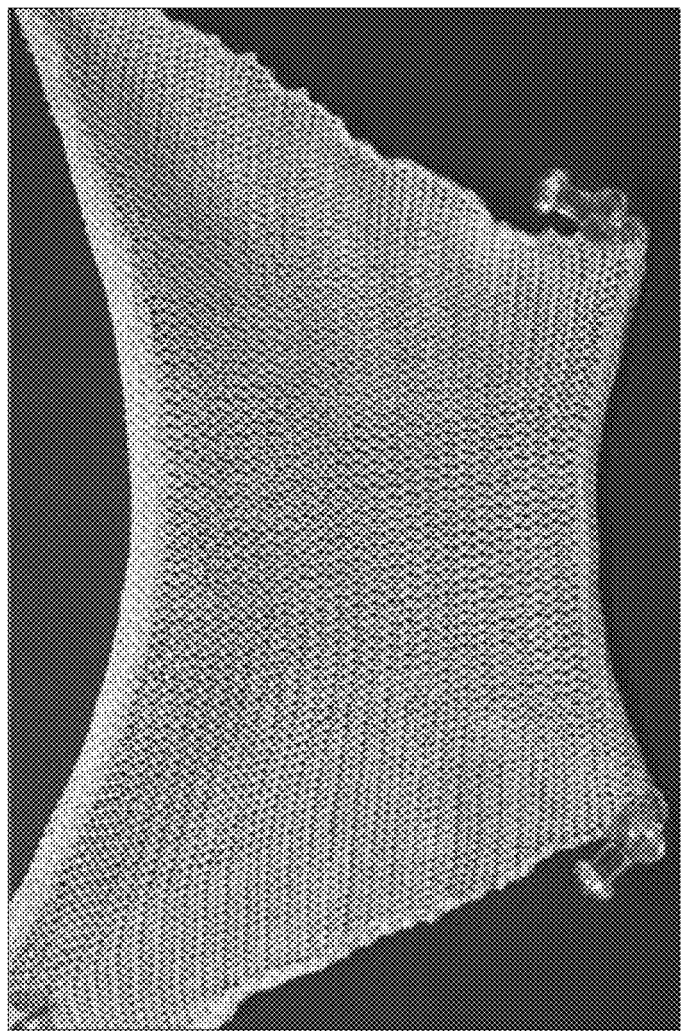
FIG. 18 illustrates yet another example mesh produced on a double needle bed weft knitting machine demonstrating shaping of the mesh for a breast support application according to aspects of the present invention.
Figure 19:
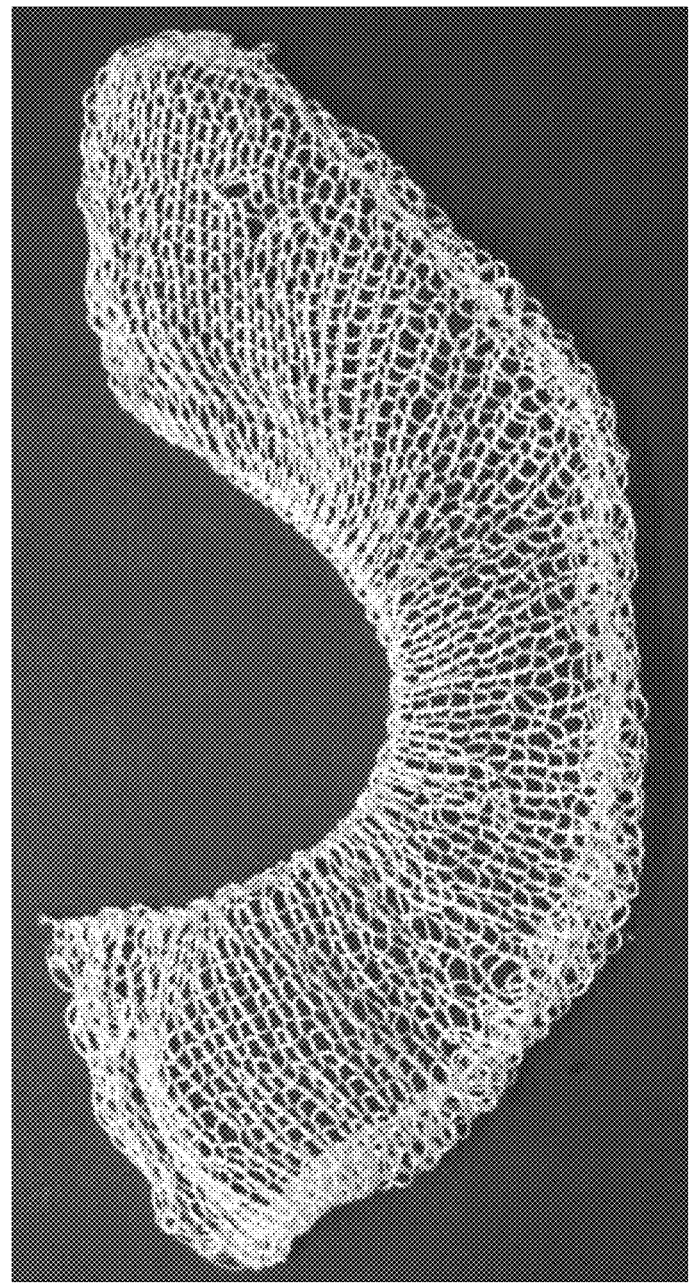
FIG. 19 illustrates a further mesh produced on a double needle bed weft knitting machine demonstrating shaping of the mesh for a breast support application according to aspects of the present invention.
Figure 20:
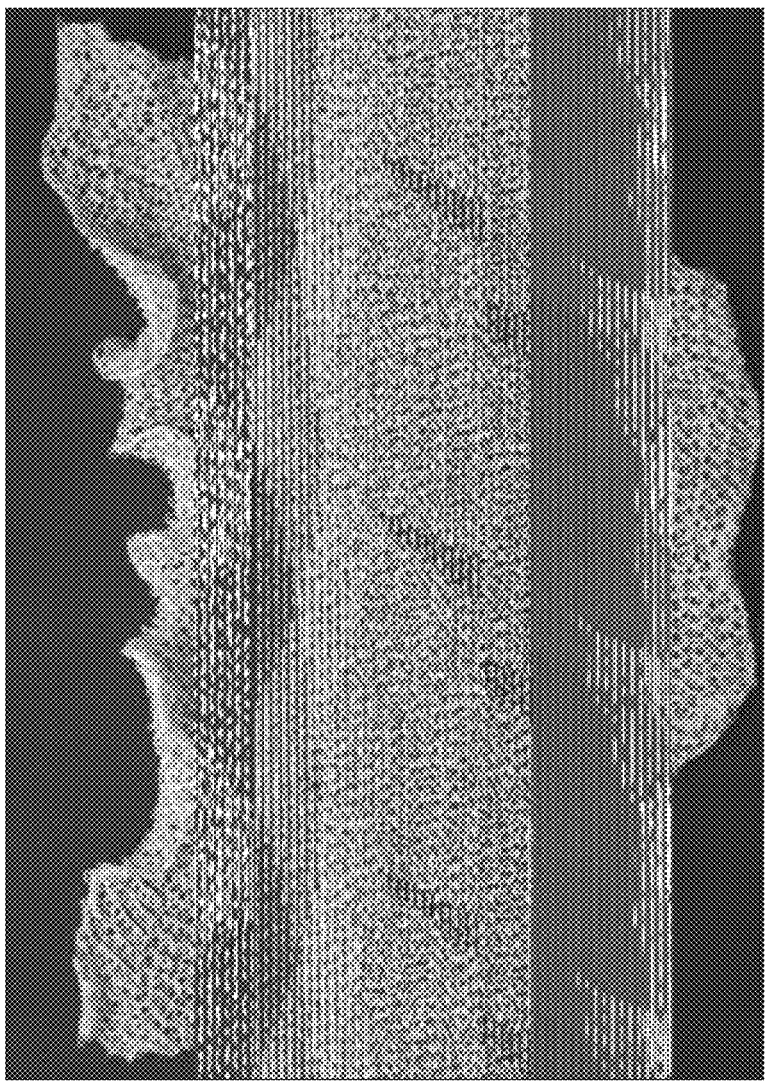
FIG. 20 illustrates another example mesh produced on a double needle bed weft knitting machine demonstrating shaping of the mesh for a breast support application according to aspects of the present invention.

FIGS. 13A-C illustrate an example non-porous mesh 1300 according to aspects of the present invention. FIG. 13A shows the technical front 1300A of the non-porous mesh 1300. FIG. 13B shows the technical back 1300B of the non-porous mesh 1300. FIG. 13C shows that non-porous mesh 1300 has a thickness of 5.87 mm.

FIG. 14A illustrates an example three-dimensional mesh 1400 with the same technical front and technical back according to aspects of the present invention. FIG. 14B shows that the three-dimensional mesh 1400 has a thickness of approximately 5.36 mm. FIGS. 15A and B illustrate another example three-dimensional mesh fabric 1500 according to aspects of the present invention. FIG. 15A shows the technical front 1500A of the fabric 1500, and FIG. 15B illustrates the technical back 1500B of the fabric 1500.

FIGS. 16-20 illustrate respective example meshes 1600, 1700, 1800, 1900, and 2000 that are produced on a double needle bed weft knitting machine. The meshes 1600, 1700, 1800, 1900, and 2000 demonstrate shaping of a mesh for a breast support application according to aspects of the present invention.

A test method was developed to check the cutability of the surgical mesh formed according to aspects of the present invention. In the test method, the surgical mesh evaluated according to the number of were needed to cut the mesh with surgical scissors. The mesh was found to cut excellently because it took one scissor stroke to cut through it. The mesh was also cut diagonally and in circular patterns to determine how easily the mesh unraveled and how much it unraveled once cut. The mesh did not unravel more than one mode after being cut in both directions. To determine further if the mesh would unravel, a suture, was passed through the closest pore from the cut edge, and pulled. This manipulation did not unravel the mesh. Thus, the surgical mesh is easy to cut and does not unravel after manipulation.

Embodiments may be processed with a surface treatment, which increases material hydrophilicity, biocompatibility, physical, and mechanical properties such as handling for ease of cutting and graft pull-through, as well as anti-microbial and anti-fungal coatings. Specific examples of surface treatments include, but are not limited to:

plasma modification
protein such as but not limited to fibronectin, denatured collagen or gelatin, collagen gels and hydrophobin by covalent link or other chemical or physical method
peptides with hydrophilic and a hydrophobic end
peptides contain one silk-binding sequence and one biologically active sequence—biodegradable cellulose
surface sulfonation
ozone gas treatment
physically bound and chemically stabilized peptides
DNA/RNA aptamers
Peptide Nucleic Acids
Avimers
modified and unmodified polysaccharide coatings
carbohydrate coating
anti-microbial coatings
anti-fungal coatings
phosphorylcholine coatings A method to evaluate the ease of delivery through a cannula was done to make sure the surgical mesh could be used laparoscopically. Various lengths were rolled up and pushed through two different standard sized cannulas using surgical graspers. The mesh was then evaluated to determine if there was any damage done to the mesh. The mesh that was put through the cannulas was found to have slight distortion to the corner that was held by the grasper. The 16 cm and 18 cm lengths of mesh that were rolled up and pushed through the 8 mm cannula had minimal fraying and one distorted pore, respectively. It was also found that no damage was done to the cannula or septum in any of the tests. It was found that appropriately sized surgical mesh will successfully pass through a laparoscopic cannula without damage, enabling its effective use during laparoscopic procedures.

A surgical mesh device according to aspects of the present invention has been found to bio-resorb by 50% in approximately 100 days. In a study by Horan et al., Sprague-Dawley rats were used to compare the bio-resorption of embodiments according to the present invention to Mersilene™ mesh (Ethicon, Somerville, N.J.). The histology reports from the article state that after 94 days, 43% of the initial mesh of the embodiments remained compared to 96% of the Mersilene™ mesh. It was also reported that the in growth was more uniform with the mesh of embodiments than the Mersilene™ mesh. The Mersilene™ was found to have less in growth in the defect region than along the abdominal wall.

Physical properties include thickness, density and pore sizes. The thickness was measured utilizing a J100 Kafer Dial Thickness Gauge. A Mitutoyo Digimatic Caliper was used to find the length and width of the samples; used to calculate the density. The density was found by multiplying the length, width and thickness of the mesh then dividing the resulting value by the mass. The pore size was found by photographing the mesh with an Olympus SZX7 Dissection Microscope under 0.8× magnification. The measurements were taken using ImagePro 5.1 software and the values were averaged over several measurements. The physical characteristics of the sample meshes, including embodiments according to the present invention, are provided in TABLE 2.

TABLE 2

| | Physical Characterization | | |
|---|---|---|---|
| Device | Thickness (mm) | Pore Size (mm$^2$) | Density (g/cm$^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| Present Embodiments-Single Needle Bed (SB) | 1.0 ± 0.04 | 0.640 ± 0.409 | 0.176 ± 0.002 |
| Present Embodiments-Double Needle Bed (DB) | 0.80 ± 0.20 | 1.27 | 0.135 ± 0.165 |

All devices were cut to the dimensions specified in TABLE 3, for each type of mechanical analysis. Samples were incubated in phosphate buffered saline (PBS) for 3±1.25 hours at 37±2° C. prior to mechanical analysis to provide characteristics in a wet environment. Samples were removed from solution and immediately tested.

TABLE 3

| Test Modality | Length (mm) | Width (mm) |
|---|---|---|
| Tensile | 60 | 10 |
| Burst | 32 | 32 |
| Suture Pull-Out | 40 | 20 |
| Tear | 60 | 40 |
| Tensile Fatigue | 60 | 40 |

Ball burst test samples were scaled down due to limitations in material dimensions. The test fixture employed was a scaled (1:2.5) version of that recommended by ASTM Standard D3787. The samples were centered within a fixture and burst with a 10 mm diameter ball traveling at a displacement rate of 60 mm/min. Maximum stress and stiffness were determined from the burst test. Results can be seen in TABLE 4.

TABLE 4

| | Burst Strength | |
|---|---|---|
| Device | Stress (MPa) | Stiffness (N/mm) |
| Mersilene Mesh | 0.27 ± 0.01 | 13.36 ± 0.85 |
| Bard Mesh | 0.98 ± 0.04 | 38.28 ± 1.49 |
| Vicryl Knitted Mesh | 0.59 ± 0.05 | 32.27 ± 1.86 |
| Pelvitex Polypropylene Mesh | 0.59 ± 0.04 | 29.78 ± 1.33 |
| Permacol Biologic Implant | 1.27 ± 0.27 | 128.38 ± 22.14 |
| Present Embodiments (SB) | 0.76 ± 0.04 | 46.10 ± 2.16 |
| Present Embodiments (DB) | 0.66 | 40.9 |

Tensile tests were performed along the fabric formation and width axes of each device. A 1 cm length of mesh on each end of the device was sandwiched between pieces of 3.0 mm thick silicone sheet and mounted in pneumatic fabric clamps with a clamping pressure of 70-85 psi. Samples were loaded through displacement controlled testing at a strain rate of 100%/s (2400 mm/min) and/or 67%/s (1600 mm/min) until failure. The ultimate tensile strength (UTS), linear stiffness and percent elongation at break can be seen in the following tables. Results can be found in TABLES 5-8. An entry of "NT" indicates that the data has not yet been tested.

TABLE 5

| | Tensile SPTF (Fabric Formation Axis-1600 mm/min) | | | |
|---|---|---|---|---|
| Device | Strength (N) | Stress (MPa) | Stiffness (N/mm) | % Elong. @ Break |
| Mersilene Mesh | 46.14 ± 3.15 | 10.04 ± 0.71 | 0.90 ± 0.06 | 132.1% ± 9.3% |
| Bard Mesh | 30.90 ± 2.0 | 16.64 ± 1.16 | 3.32 ± 0.26 | 106.5% ± 3.2% |
| Vicryl Knitted Mesh | 35.69 ± 3.30 | 35.89 ± 4.48 | 2.59 ± 0.33 | 89.0% ± 7.3% |
| Present Embodiments (SB) | 76.72 ± 4.36 | 10.06 ± 0.38 | 7.13 ± 0.50 | 41.5% ± 2.3% |
| Present Embodiments Mesh (DB) | NT | NT | NT | NT |

TABLE 6

| | Tensile SPTF (Fabric Formation Axis-2400 mm/min) | | | |
|---|---|---|---|---|
| Device | Strength (N) | Stress (MPa) | Stiffness (N/mm) | % Elong. @ Break |
| Mersilene Mesh | 43.87 ± 5.19 | 14.15 ± 1.68 | 2.18 ± 0.3 | 56.6% ± 3.5% |
| Bard Mesh | 35.29 ± 5.69 | 4.90 ± 0.79 | 0.80 ± 0.23 | 177.3% ± 13.2% |
| Vicryl Knitted Mesh | 30.88 ± 3.30 | 14.04 ± 1.50 | 0.76 ± 0.17 | 191.9% ± 14.2% |
| Pelvite Polypropylene Mesh | 23.05 ± 3.75 | 5.36 ± 0.87 | 0.57 ± 0.07 | 110.0% ± 13.6% |
| Permacol Biologic Implant | 164.52 ± 30.58 | 13.71 ± 2.55 | 23.94 ± 2.7 | 23.5% ± 3.3% |
| Present Embodiments (SB) | 72.31 ± 7.80 | 6.95 ± 0.75 | 4.31 ± 0.3 | 45.5% ± 5.2% |
| Present Embodiments (DB) | 74.62 ± 2.70 | 8.68 ± 0.31 | 4.25 ± 0.13 | 48.3% ± 2.1% |

TABLE 7

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 31.14 ± 2.21 | 10.04 ± 0.71 | 0.90 ± 0.06 | 132.1% ± 9.3% |
| Bard Mesh | 119.80 ± 8.36 | 16.64 ± 1.16 | 3.32 ± 0.26 | 106.5% ± 3.2% |
| Vicryl Knitted Mesh | 78.96 ± 9.86 | 35.89 ± 4.48 | 2.59 ± 0.33 | 89.0% ± 7.3% |
| Present Embodiments (SB) | 104.58 ± 3.96 | 10.06 ± 0.38 | 7.13 ± 0.50 | 41.5% ± 2.3% |
| Present Embodiments (DB) | NT | NT | NT | NT |

TABLE 8

Tensile SPTF (Fabric Width Axis-2400mm/min)

| Device | Strength (N) | Stress (MPa) | Stiffness (N/mm) | % Elong. @ Break |
|---|---|---|---|---|
| Mersilene Mesh | 28.11 ± 2.93 | 28.11 ± 2.93 | 1.05 ± 0.13 | 128.2% ± 23.6% |
| Bard Mesh | 103.53 ± 8.92 | 14.38 ± 1.24 | 3.43 ± 0.5 | 94.0% ± 8.4% |
| Vicryl Knitted Mesh | 106.65 ± 8.46 | 48.48 ± 3.85 | 5.08 ± 0.1 | 58.6% ± 8.4% |
| Pelvite Polypropylene Mesh | 30.24 ± 5.77 | 7.03 ± 1.34 | 1.48 ± 0.1 | 89.6% ± 9.6% |
| Permacol Biologic Implant | 67.71 ± 13.36 | 5.64 ± 1.11 | 8.56 ± 2.0 | 27.4% ± 4.2% |
| Present Embodiments (SB) | 98.84 ± 4.79 | 9.50 ± 0.46 | 8.48 ± 0.3 | 39.0% ± 4.1% |
| Present Embodiments (DB) | 70.08 ± 2.55 | 8.15 ± 0.30 | 5.87 ± 0.22 | 33.6% ± 2.0% |

Tear Strength was found through a method that entailed cutting a 10 mm "tear" into the edge, perpendicular to the long axis edge and centered along the length of the mesh. The mesh was mounted in pneumatic fabric clamps as previously described in the tensile testing methods. Samples were loaded through displacement controlled testing at a strain rate of 100%/s (2400 mm/min) until failure. The load at failure and the mode of failure are shown in TABLE 9.

TABLE 9

| Device | Tear Strength Strength (N) | Failure Mode |
|---|---|---|
| Mersilene Mesh | 110.30 ± 5.63 | Tear Failure: 6/6 |
| Bard Mesh | 181.70 ± 12.33 | Tear Failure: 6/6 |
| Vicryl Knitted Mesh | 109.35 ± 4.85 | Tear Failure: 6/6 |
| Pelvitex Polypropylene Mesh | 108.14 ± 6.95 | Tear Failure: 4/6 |
| Permacol Biologic Implant | 273.79 ± 65.57 | Tear Failure: 6/6 |
| Embodiments (SB) | 194.81 ± 9.12 | Tear Failure: 6/6 |
| Embodiments (DB) | NT | NT |

Tensile fatigue testing was performed on the surgical mesh device according to aspects of the present invention and representative predicate types including Vicryl Mesh and Bard Mesh. Samples were loaded into the pneumatic fabric clamps as previously described in the tensile testing methods above. Samples were submerged in PBS at room temperature during cycling. Sinusoidal load controlled cycling was preformed to 60% of mesh ultimate tensile strength. Number of cycles to failure was determined during the cyclic studies and can be seen in TABLE 10, where failure was indicated by fracture or permanent deformation in excess of 200%.

TABLE 10

| Device | Tensile Fatigue Cycles, 60% UTS |
|---|---|
| Bard Mesh | 6994 ± 2987 |
| Vicryl Knitted Mesh | 91 ± 127 |
| Embodiments (DB) | 1950 ± 1409 |

A method was developed to compare the suture pull out strength of the surgical mesh device according to aspects of the present invention to other surgical mesh on the market. Tested mesh was sutured with three 3.5 mm diameter suture anchors (Arthrex, Naples, Fla.) and secured to 15 pcf solid rigid polyurethane foam. Each device was positioned with the center of the 20 mm width over the center anchor with a 3 mm suture bite distance employed during suturing of the mesh to the 3 anchors. The saw bone was mounted in the lower pneumatic fabric clamp and offset to provide loading along the axis of the device when the device was centered under the load cell. The free end of the mesh was sandwiched between the silicone pieces and placed in the upper fabric clamp with 85±5 psi clamping force. Testing was performed under displacement control with a strain rate of 100%/s (1620 mm/min). Maximum load at break and failure mode can be seen in TABLE 11.

TABLE 11

| Device | Suture-Pull-Out | |
|---|---|---|
| | Strength/Suture [N] | Failure Mode |
| Mersilene Mesh | 13.50 ± 1.65 | Mesh Failure: 6 of 6 |
| Bard Mesh | 28.80 ± 3.39 | Mesh Failure: 6 of 6 |
| Vicryl Knitted Mesh | 12.90 ± 1.30 | Mesh Failure: 6 of 6 |
| Pelvitex Polyproplene Mesh | 18.29 ± 4.04 | Mesh Failure: 6 of 6 |
| Permacol Biologic Implant | 47.36 ± 7.94 | Mesh Failure: 6 of 6 |
| Embodiments (SB) | 41.00 ± 2.98 | Mesh Failure: 6 of 6 |
| Embodiments (DB) | 32.57 ± 2.30 | Mesh Failure: 6 of 6 |

By utilizing the pattern for the double needle bed mesh and modifying the yarn size, yarn feed rate and/or needle bed width, the surgical mesh device according to aspects of the present invention would meet the physical and mechanical properties necessary for a soft or hard tissue repair depending on the application. Such properties include pore size, thickness, ultimate tensile strength, stiffness, burst strength and suture pull out. The pore size could be modified dependent to the feed rate to create a more open fabric and the thickness could range from 0.40 mm up to as wide as 19.0 mm. With modifications to the pore size and thickness the UTS, stiffness, burst strength and suture pull out would all be modified as well, most likely tailoring the modifications of the pore size and/or thickness to meet certain mechanical needs.

This mesh, created on the flat knitting machine would be made in such a way to increase or decrease pore size and/or thickness by changing the yarn size and/or changing the loop length found within the knitting settings. The loop placements in combination with the node lock design allow changes to the shape and/or to the mechanical properties of the mesh. A biocompatible yarn with elasticity, such as highly twisted silk, could be used for shaping.

Figure 21A:
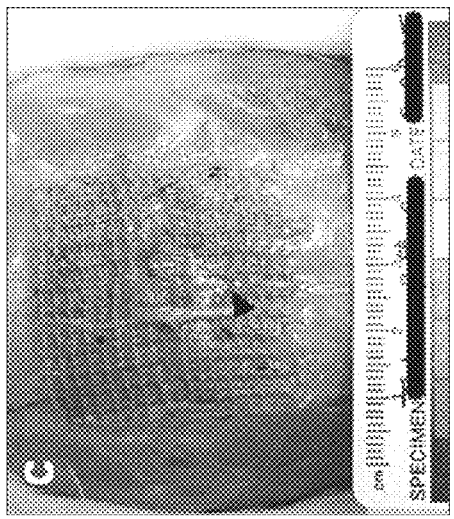
FIG. 21A illustrates a full-thickness rat abdominal defect created using a custom designed 1-cm stainless steel punch, the defect appearing oval in shape due to body wall tension applied.
Figure 21D:
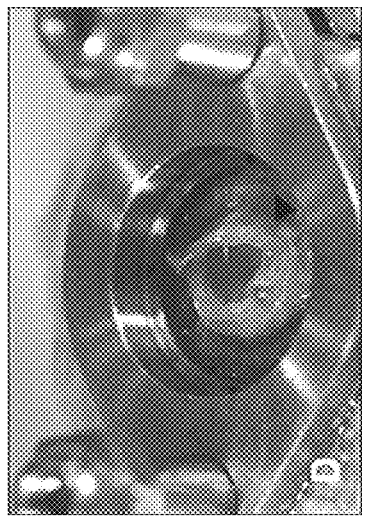
FIG. 21D illustrates ball burst testing performed with a 1-cm diameter ball pushed through the defect site reinforced with the mesh according to aspects of the present invention.
Figure 21A:
Figure 21B:
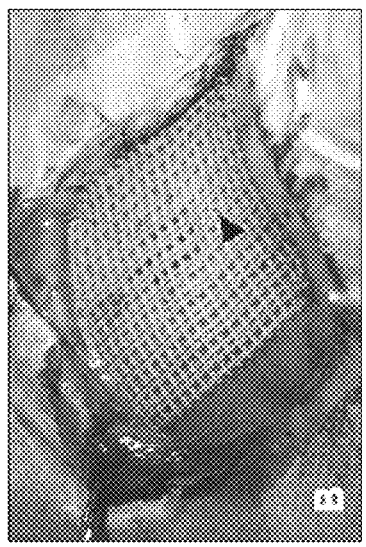
FIG. 21B illustrates a 4 cm×4 cm example implant centered on top of the open defect of FIG. 21A, and held in place with single interrupted polypropylene sutures (arrow) through the implant and muscle.

The implantation of a mesh and subsequent testing according to aspects of the present invention is illustrated in FIGS. 21A-D. FIG. 21A illustrates a full-thickness rat abdominal defect created using a custom designed 1-cm stainless steel punch. The defect appears oval in shape due to body wall tension applied. FIG. 21B illustrates a 4 cm×4 cm implant centered on top of the open defect, and held in place with single interrupted polypropylene sutures (arrow) through the implant and muscle. FIG. 21C illustrates an explanted specimen 94 days post implantation. FIG. 21D illustrates ball burst testing performed with a 1-cm diameter ball pushed through the defect site reinforced with the mesh.

While the present invention has been described in connection with a number of exemplary embodiments, and implementations, the present inventions are not so limited, but rather cover various modifications, and equivalent arrangements. For example, a knitted mesh according to aspects of the present invention may be used for a filler material. In one application, the knitted mesh may be cut into 1 mm×1 mm sections to separate one or more nodes, e.g., 3 nodes. The sections may be added to fat tissue or a hydro-gel to form a solution that can be injected into a defective area. Advantageously, the filler material may provide a desired texture, but will not unravel.

Figure 28:
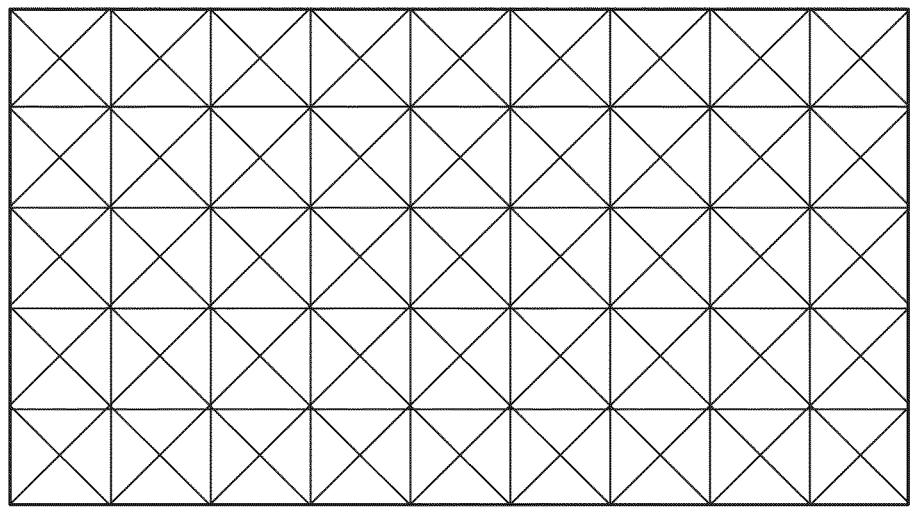
FIG. 28 illustrates a scaffold with diagonal members at 45 degrees.
Figure 29:
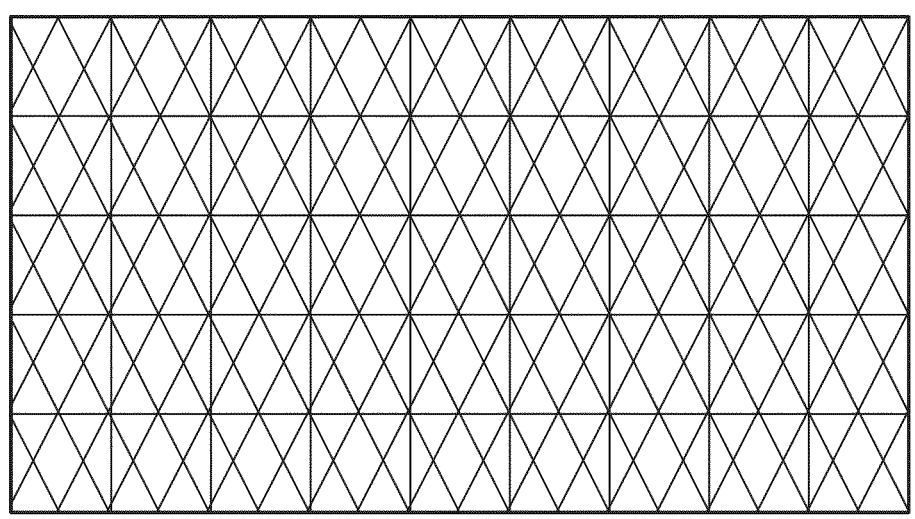
FIG. 29 illustrates a scaffold with diagonal members at 60 degrees.

In an aspect of the present invention, a knitted scaffold or mesh that comprises diagonal or crossing yarn members. Preferably, the knitted scaffold is comprised of silk. In still yet another aspect of the present invention, the diagonal or crossing yarn members are used in combination with a node-lock scaffold construction. Diagonal yarn members, at varying angles, are added to a silk scaffold design, as shown in FIGS. 28 and 29. FIG. 28 illustrates a scaffold with diagonal members at 45 degrees. FIG. 29 illustrates a scaffold with diagonal members at 60 degrees. In an aspect of the present invention, adding the diagonal yarn members also provides the knitted scaffold with a memory such that the knitted scaffold is capable of retaining a particular shape.

Figure 30:
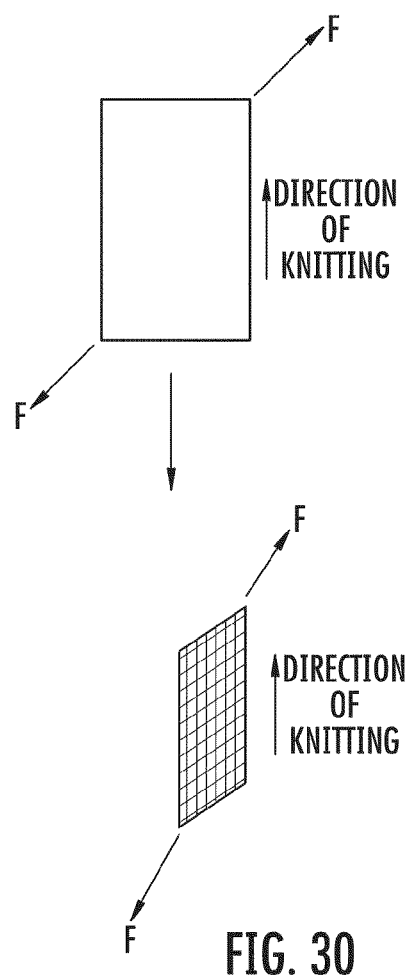
FIG. 30 illustrates collapse of a scaffold when opposing forces are applied at an angle from the direction of knitting.
Figure 31:
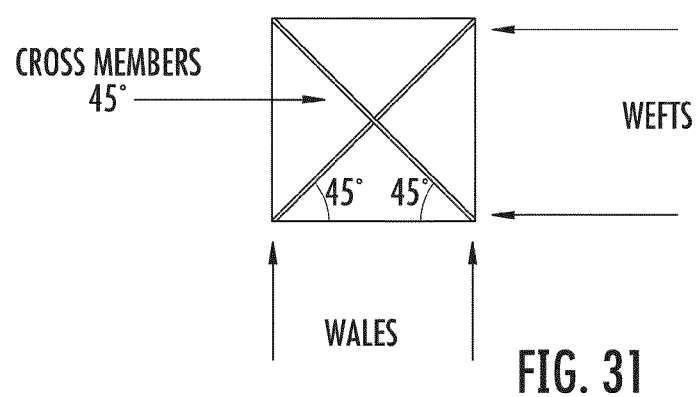
FIG. 31 illustrates a yarn member placed in the direction of knitting at a 45 degree angle from the wale or weft direction at opposing corners of a pore according to aspects of the present invention.

Thus, the present invention relates to a knitted scaffold structure and a method to resist the collapse of the scaffold when opposing forces are applied at an angle from the direction of knitting as illustrated in FIG. 30. When force is applied at an angle, the scaffold tends to collapse because there are no load bearing members. The scaffold becomes deformed and thereby shrinks as shown in FIG. 30. Diagonal or crossing yarn members may be used to stiffen a scaffold when a diagonal load is applied. These members also make the scaffold more homogeneous so that the risk of implanting the scaffold in the wrong orientation is eliminated. The use of the diagonal yarn members addresses the collapse of a mesh or scaffold when opposing forces are applied at an angle such as 45 degrees from the direction of knitting. In accordance with an aspect of the present invention, a member is placed in the direction of knitting (such as 45 degrees from the wale or weft direction) at approximately opposing corners of a pore shown in FIG. 31.

Figure 32:
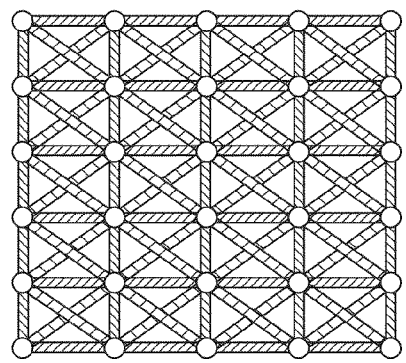
FIG. 32 illustrates diagonal yarns applied as load bearing members in a scaffold according to aspects of the present invention.
Figure 33:
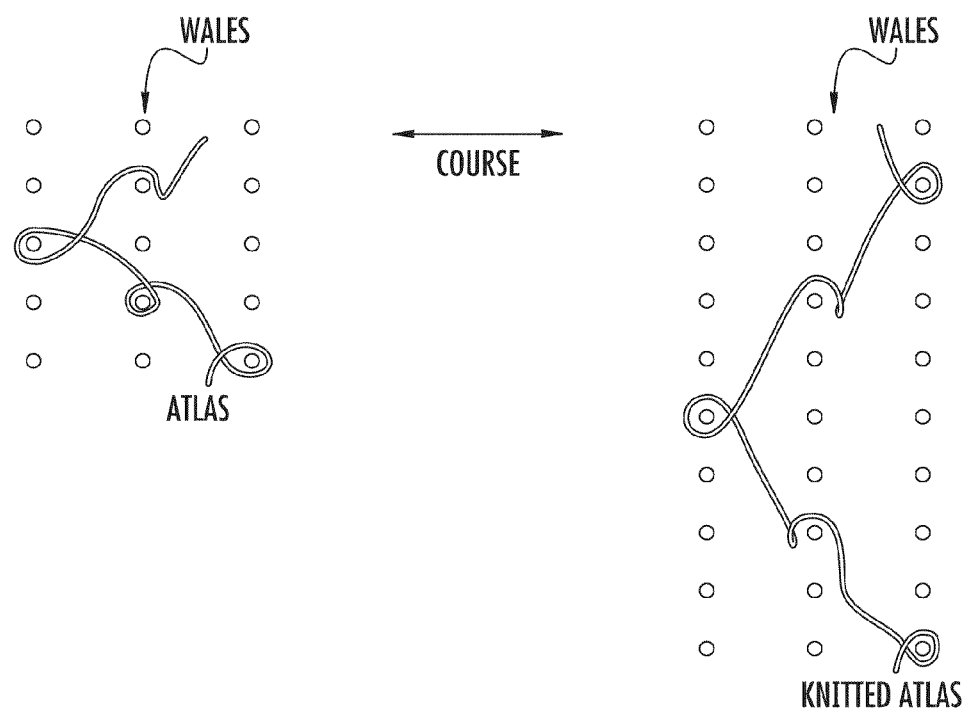
FIG. 33 illustrates a yarn evolution with diagonal yarn members according to aspects of the present invention.

FIG. 32 illustrates diagonal yarns applied as load bearing members in a scaffold in accordance with the present invention. As shown in FIG. 33, the 45 degree diagonal members could be made with a yarn evolution similar to an atlas out with N-number of courses with no knit, for example, enough until the next node at the corner of a pore.

Figure 34:
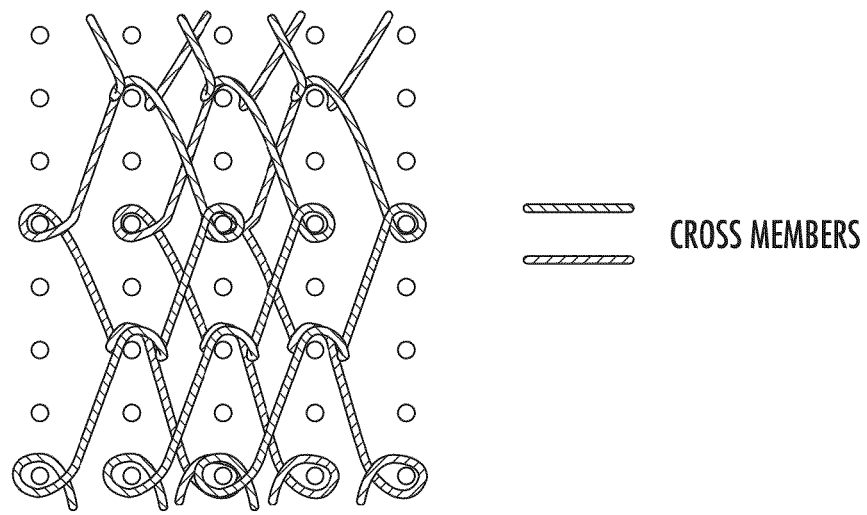
FIG. 34 illustrates use of two bars in opposing directions according to aspects of the present invention.

In order to provide a continuous support across the width of the fabric, two bars may be used in opposing directions as shown in FIG. 34.

Figure 35:
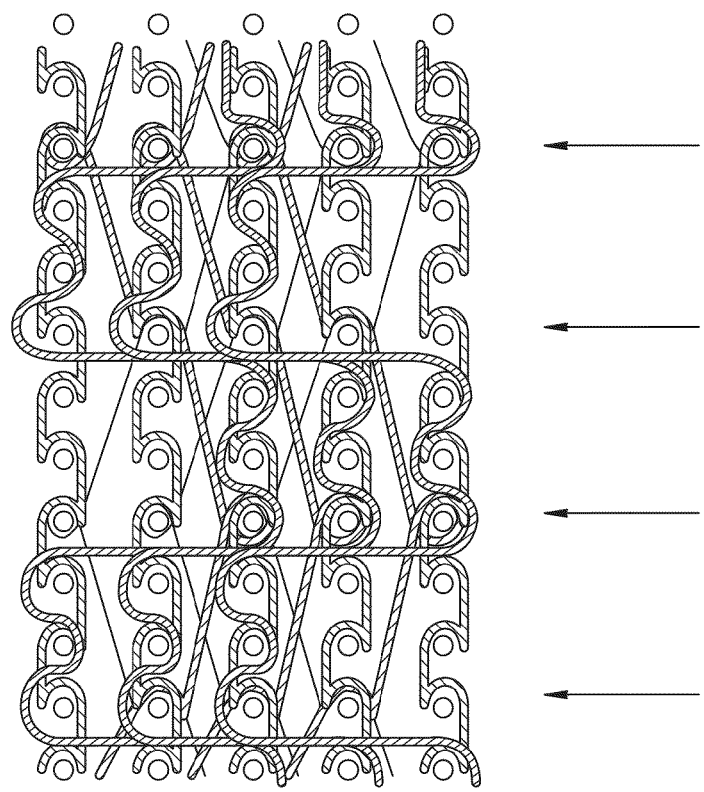
FIG. 35 illustrates three warp yarns on the same needle according to aspects of the present invention.
Figure 36:
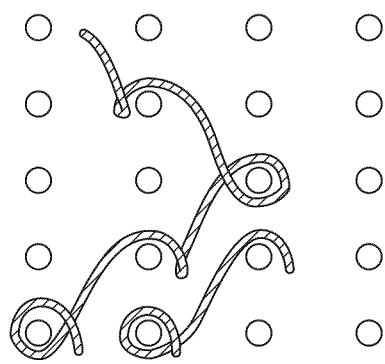
FIG. 36 illustrates the warp of a vertical yarn replaced with a weft insertion movement in place of an open stitch according to aspects of the present invention.

By using the node-lock design in combination with the diagonal yarn members, the resulting yarn evolution is as illustrated in FIG. 35. FIG. 35 illustrates 3 warp yarns on the same needle. However, the warp of the vertical yarn may be replaced with a weft insertion movement in place of the open stitch, as shown in FIG. 36.

Figure 37:
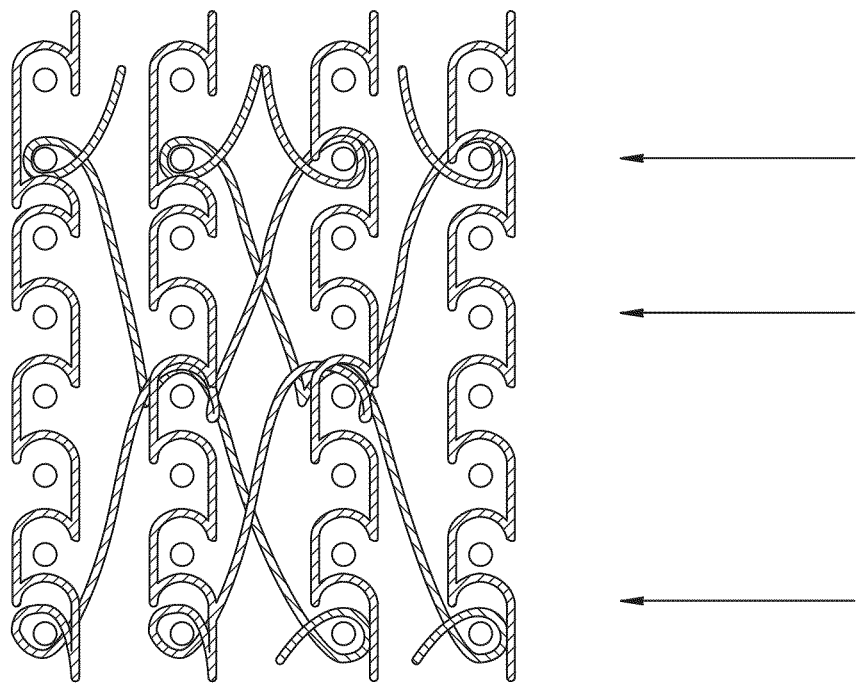
FIG. 37 illustrates no loops formed by warp yarns according to aspects of the present invention.

FIG. 37 illustrates no loops formed by warp yarns.

Figure 38:
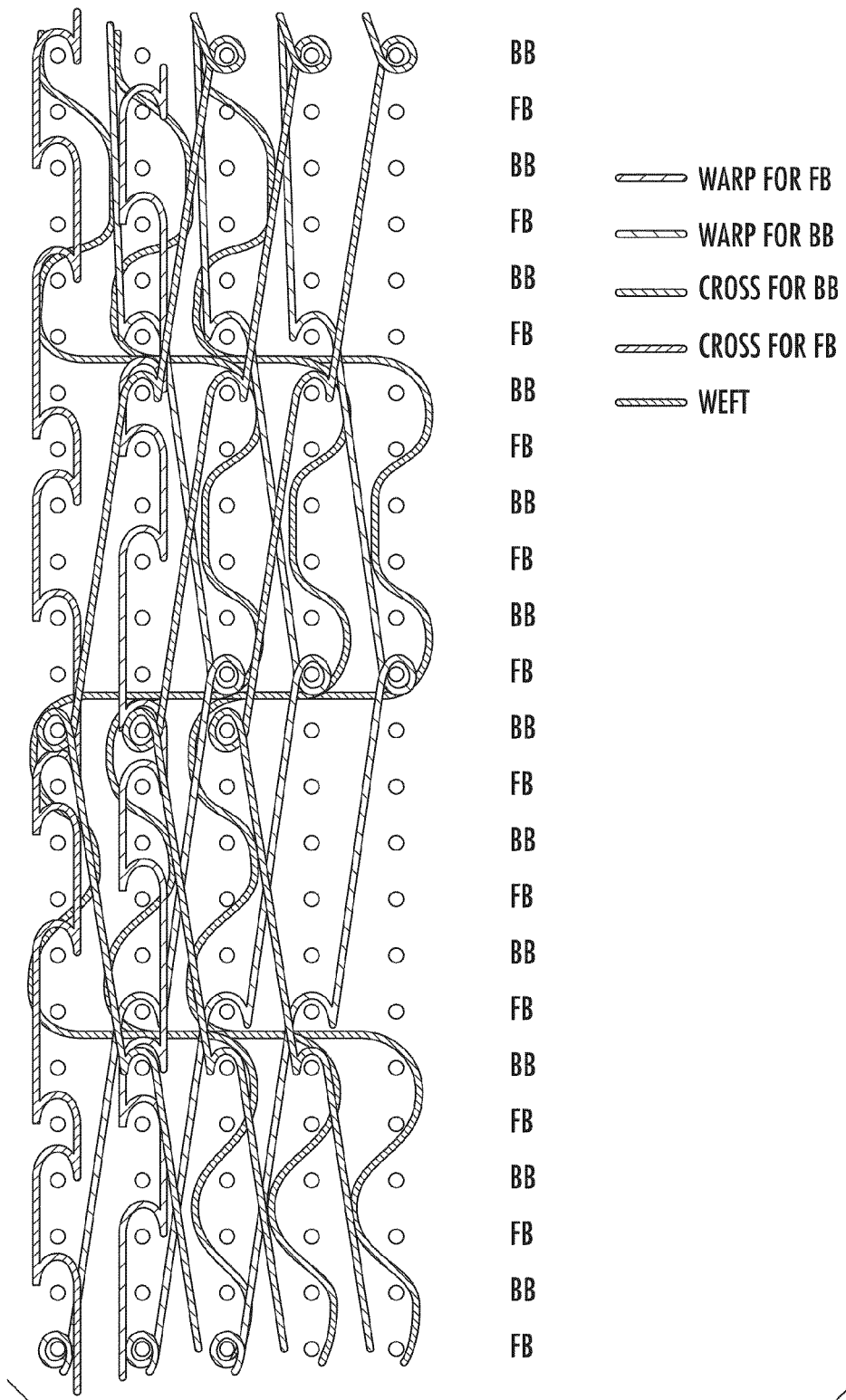
FIG. 38 illustrates a double needle bed node lock design with diagonal yarn members according to aspects of the present invention.
Figure 39:
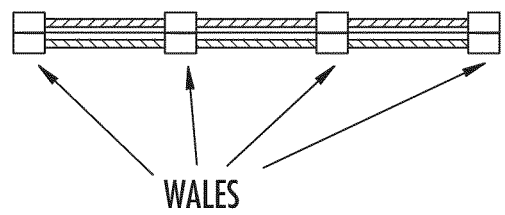
FIG. 39 illustrates a cross-section of the resulting scaffold results on top of the weft toward the surface of the scaffold according to aspects of the present invention.

All of the previous designs are meant to be reproduced on a single needle bed machine. The same principle applies to a double needle bed construction. For example, in FIG. 38 is represented a double needle bed node lock design with diagonal yarn members. As shown in FIG. 38, one cross yarn works on the back needle bed while the other cross yarn works on the front bed only. As shown in FIG. 39, the cross-section of the resulting scaffold results on top of the weft toward the surface of the mesh or scaffold. As a result, the scaffold surface has a softer touch and is less rib-like.

Figure 40:
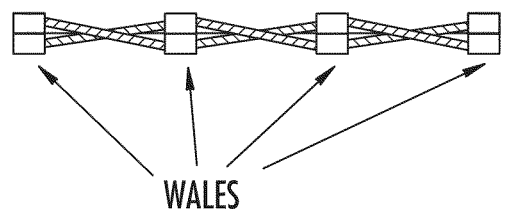
FIG. 40 illustrates a series of cross-members connecting two opposing faces of the fabric according to aspects of the present invention.

Changes to the scaffold patterns provide a series of cross-members connecting two opposing faces of the fabric as shown in FIG. 40. It is possible to make the yarns cross on two different planes forming an "X" as opposed to working on one side of the fabric and staying in the same plane as shown in FIG. 39.

Figure 41:
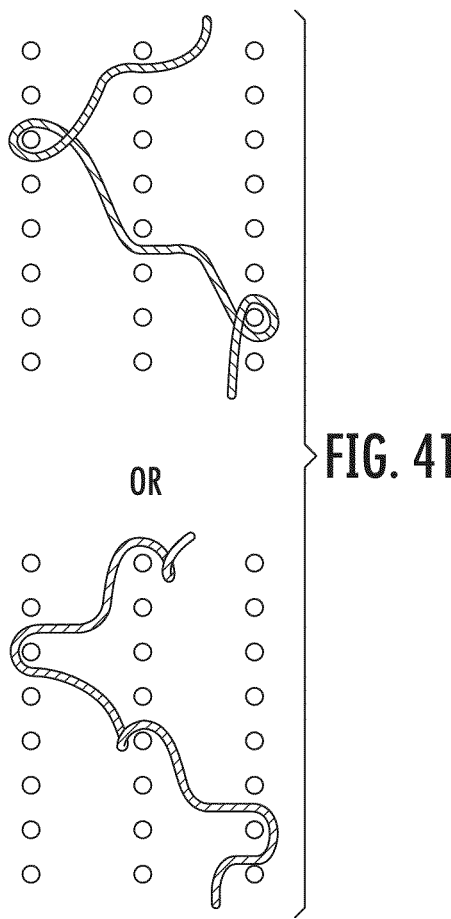
FIG. 41 illustrates a weft insertion to make the fabric more drapable according to aspects of the present invention.

The cross-members may also not form a loop by a simple weft insertion to make the fabric more drapable as shown in FIG. 41. It is also possible that the additional yarn member itself may not have to be node-lock.

For example, the weft insertion bar may be eliminated and the pores are formed by the knitting bars. Thus, two bars can achieve the same node-lock result by moving in opposite directions to each other and no weft insertion involved.

Figure 42:
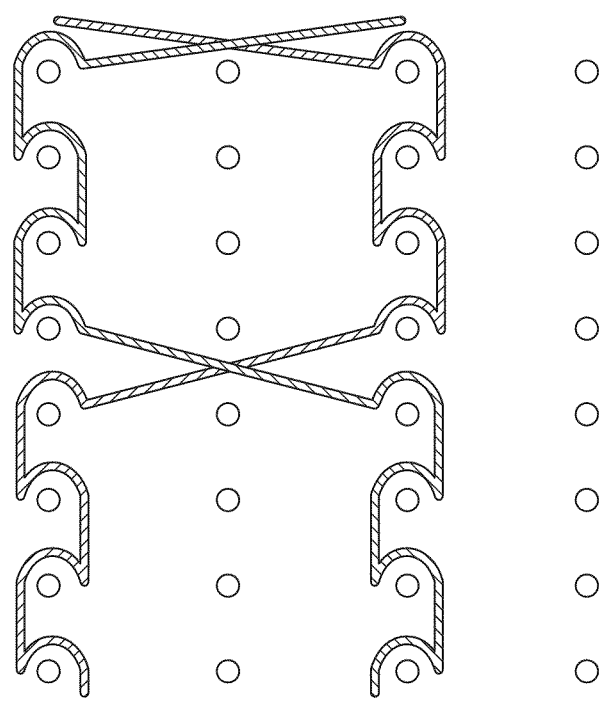
FIG. 42 illustrates a scaffold with a single needle bed construction according to aspects of the present invention.

FIG. 42 is simplified for a single needle bed construction. Similar results may be achieved with a double needle bed construction.

Thus, the present invention provided a method of using the knitted scaffold having a diagonal member as discussed herein in surgery. The surgical method(s) comprises implanting in a patient or affixing to a patient a knitted scaffold comprised of at least two silk yarns in a knit direction and having a yarn member diagonal to the knit direction. As discussed above, the diagonal yarn member is at a 45 degree to 60 degree angle from the knit direction. The implanted or affixed knitted scaffold having the diagonal yarn member provides load bearing support.

What is claimed is:

1. A knitted silk scaffold comprising:
 (a) a first set of yarns and a second set of yarns, the first set of yarns interlacing with the second set of yarns to define nodes, the first set of yarns and the second set of yarns alternately applied in a wale direction to form staggered loops, wherein the alternating application of the first set of yarns and the second set of yarns causes the first set of yarns to have different tensions relative to the second set of yarns at the nodes, and the difference in tension substantially preventing the knitted scaffold from unraveling at the nodes; and
 (b) a third set of yarns diagonal to a knit direction of the first and second set of yarns, to assist scaffold shape retention;
 wherein each of the first set of yarns, the second set of yarns, and the third set of yarns consist essentially of a sericin-depleted silk.

2. The knitted scaffold according to claim 1, wherein the diagonal yarns are at a 45 degree to 60 degree angle from the knit direction.

3. The knitted scaffold according to claim 1, wherein the diagonal yarns are in a single plane.

4. The knitted scaffold according to claim 1, wherein the diagonal yarns are in two planes.

5. The knitted scaffold according to claim 1, wherein the first set of yarns and the second set of yarns have different diameters.

6. The knitted scaffold according to claim 1, wherein the first set of yarns and the second set of yarns have different elastic properties.

* * * * *

UNITED STATES PATENT AND TRADEMARK OFFICE
CERTIFICATE OF CORRECTION

PATENT NO.         : 9,204,954 B2                                   Page 1 of 1
APPLICATION NO.    : 13/093651
DATED              : December 8, 2015
INVENTOR(S)        : Enrico Mortarino It is certified that error appears in the above-identified patent and that said Letters Patent is hereby corrected as shown below:

In the specification

In column 1, line 9, delete "Mar. 26, 2010," and insert -- Sep. 19, 2011, --, therefor.

In column 1, line 33, delete "Synecture" and insert -- Syneture --, therefor.

In column 10, line 35, delete "Gomez;" and insert -- Comez; --, therefor.

In column 10, line 36, delete "Jakkob" and insert -- Jakob --, therefor.

In column 10, line 36, delete "A G;" and insert -- AG; --, therefor.

In column 10, line 38, delete "the" and insert -- Yhe --, therefor.

In column 10, line 56, delete "Tiger;" and insert -- Tiger --, therefor.

In column 10, line 57, delete "G & P" and insert -- G & P; --, therefor.

In columns 13-14, line 8 (TABLE 6), delete "Pelvite" and insert -- Pelvitex --, therefor.

In columns 15-16, line 8 (TABLE 8), delete "Pelvite" and insert -- Pelvitex --, therefor.

In column 15, line 66, delete "preformed" and insert -- performed --, therefor.

In column 17, line 6 (TABLE 11), delete "Polyproplene" and insert -- Polypropylene --, therefor.

Signed and Sealed this
Twenty-fourth Day of May, 2016

Michelle K. Lee
*Director of the United States Patent and Trademark Office*